(12) United States Patent
Oren et al.

(10) Patent No.: US 7,943,806 B2
(45) Date of Patent: May 17, 2011

(54) PROCESS OF PREPARING BROMOPICRIN

(75) Inventors: Jakob Oren, Nesher (IL); Leah Golan, Kiryat-Yam (IL); Ron Frim, Haifa (IL)

(73) Assignee: Bromine Compounds Ltd., Beer-Sheva (IL)

( * ) Notice: Subject to any disclaimer, the term of this patent is extended or adjusted under 35 U.S.C. 154(b) by 496 days.

(21) Appl. No.: 11/989,585

(22) PCT Filed: Aug. 22, 2006

(86) PCT No.: PCT/IL2006/000978
§ 371 (c)(1),
(2), (4) Date: Jan. 28, 2008

(87) PCT Pub. No.: WO2007/023496
PCT Pub. Date: Mar. 1, 2007

(65) Prior Publication Data
US 2010/0152501 A1 Jun. 17, 2010

Related U.S. Application Data

(60) Provisional application No. 60/711,272, filed on Aug. 26, 2005.

(51) Int. Cl.
*C07C 205/00* (2006.01)
(52) U.S. Cl. .................................. 568/946
(58) Field of Classification Search .............. 568/946
See application file for complete search history.

(56) References Cited

U.S. PATENT DOCUMENTS

| | | |
|---|---|---|
| 3,159,686 A | 12/1964 | Burk et al. |
| 3,445,576 A | 5/1969 | Kenaga et al. |
| 3,929,723 A | 12/1975 | Freedman et al. |
| 4,039,731 A | 8/1977 | Freedman et al. |
| 5,013,762 A | 5/1991 | Smith et al. |
| 5,043,489 A | 8/1991 | Nocito et al. |
| 5,397,804 A | 3/1995 | Hirashima et al. |
| 5,411,990 A | 5/1995 | Tsuji et al. |
| 2007/0249501 A1 | 10/2007 | Frim et al. |

FOREIGN PATENT DOCUMENTS

| | | |
|---|---|---|
| JP | 09-067212 | 3/1997 |
| WO | WO 94/01391 | 1/1994 |
| WO | WO 2006/061842 | 6/2006 |
| WO | WO 2008/146277 | 12/2008 |

OTHER PUBLICATIONS

Bromopicrin (tribromonitromethane) [464-10-8] M 297.8, m 10.2-10.3, b 85-87, steam distil it, dry it, dry it with sodium solfate and distil it again in a vacuum, [ Beilstein 1 H 77, 1 II 43, I III 115, I IV 106].*
Official Action Dated Aug. 7, 2009 From the Ministry of Education and Science, Department of Intellectual Property of Ukraine Re.: Application No. 200803490 and Its Translation Into English.
Response Dated Oct. 18, 2009 to Office Action of Aug. 6, 2009 From the State Intellectual Property Office of the People's Republic of China Re.: Application No. 200580047583.2.
International Preliminary Report on Patentability Dated Mar. 6, 2008 From the International Bureau of WIPO Re.: Application No. PCT/IL2006/000978.
International Preliminary Report on Patentability Dated Jun. 21, 2007 From the International Bureau of WIPO Re.: Application No. PCT/IL2005/001330.
Examination Report Dated Jun. 5, 2009 From the Intellectual Property Office of New Zealand Re.: Application No. 556062.
International Search Report and the Written Opinion Dated Aug. 2, 2006 From the International Searching Authority Re.: Application No. PCT/IL05/01330.
International Search Report Dated May 16, 2007 From the International Searching Authority Re.: Application No. PCT/IL06/00978.
Translation of Notice of Division of Application Dated Aug. 6, 2009 From the State Intellectual Property Office of the People's Republic of China Re.: Application No. 200580047583.2.
Written Opinion Dated May 16, 2007 From the International Searching Authority Re.: Application No. PCT/IL06/00978.
International Search Report Dated Oct. 15, 2008 From the International Searching Authority Re.: Application No. PCT/IL2008/000712.
Supplementary European Search Report and European Search Opinion Dated Oct. 15, 2008 From the European Patent Office Re.: Application No. 06796066.6.
Written Opinion Dated Oct. 15, 2008 From the International Searching Authority Re.: Application No. PCT/IL2008/000712.
Juby et al. "The Origin of Carbon Atoms 2, 3, and 7 of Ricinine", Canadian Journal of Chemistry, XP002498043, 41: 117-122, 1963. p. 117, Compound VIII.
Official Action Dated Jun. 7, 2010 From the Ministry of Education and Science, Department of Intellectual Property of Ukraine Re.: Application No. 200803490 and Its Translation Into English.
Response Dated Aug. 2, 2010 to Official Action Dated Jun. 7, 2010 From the Ministry of Education and Science, Department of Intellectual Property of Ukraine Re.: Application No. 200803490.
Office Action Dated Oct. 27, 2010 From the Israel Patent Office Re. Application No. 183821 and Its Translation Into English.
Response Dated Nov. 18, 2010 to Official Action of Jul. 20, 2010 From the US Patent and Trademark Office Re.: U.S. Appl. No. 11/808,492.

(Continued)

*Primary Examiner* — Jafar Parsa

(57) ABSTRACT

Process of preparing high purity bromopicrin, and high purity bromopicrin produced therefrom. Providing a mixture of nitromethane and bromine, and preferably water, and absent of organic solvent. Adding an aqueous solution of an alkaline substance to the mixture, thereby providing a reaction mixture containing bromopicrin, the adding performed such that no excess of the alkaline substance occurs in the reaction mixture during the adding. Collecting the organic phase (containing the bromopicrin) from the reaction mixture. No need for subjecting the organic phase of the reaction mixture to distillation or extraction, for obtaining near quantitative yield of bromopicrin having purity of at least equal to or greater than 96 weight percent. Process parameters controlling selectivity of reaction forming bromopicrin are molar ratio of bromine and nitromethane in the mixture; reaction temperature while bromopicrin is formed; concentration of the alkaline substance in the aqueous solution; and reaction time.

26 Claims, 2 Drawing Sheets

OTHER PUBLICATIONS

Response Dated Nov. 28, 2010 to Examination Report of Apr. 23, 2010 From the Intellectual Property Office of New Zealand Re.: Application No. 556062.
Translation of Office Action Dated Oct. 27, 2010 From the State Intellectual Property Office of the People's Republic of China Re. Application No. 200680030435.4.
International Preliminary Report on Patentability Dated Dec. 1, 2009 From the International Bureau of WIPO Re.: Application No. OPCT/IL2008/000712.
Official Action Dated Dec. 14, 2009 From the US Patent and Trademark Office Re.: U.S. Appl. No. 11/808,492.
Response Dated Jan. 14, 2010 to Official Action of Dec. 14, 2009 From the US Patent and Trademark Office Re.: U.S. Appl. No. 11/808,492.
Response Dated Feb. 16, 2010 to Official Action of Aug. 18, 2009 From the Ministry of Education and Science, Department of Intellectual Property of Ukraine Re.: Application No. 200803490.
Response Dated Mar. 17, 2010 to Examination Report of Jun. 5, 2009 From the Intellectual Property Office of New Zealand Re.: Application No. 556062.
Translation of Office Action Dated Jan. 22, 2010 From the State Intellectual Property Office of the Peoples Republic of China Re.: Application No. 200580047583.2.
Official Action Dated Apr. 22, 2010 From the US Patent and Trademark Office Re.: U.S. Appl. No. 11/808,492.
Official Action Dated Jul. 20, 2010 From the US Patent and Trademark Office Re.: U.S. Appl. No. 11/808,492.
Examination Report Dated Apr. 23, 2010 From the Intellectual Property Office of New Zealand Re.: Application No. 584731.
Examiner's Report Dated Apr. 23, 2010 From the Australian Government, IP Australia Re. Application No. 2005312894.
Response Dated May 24, 2010 to Official Action of Apr. 22, 2010 From the US Patent and Trademark Office Re.: U.S. Appl. No. 11/808,492.
Examination Report Dated Apr. 23, 2010 From the Intellectual Property Office of New Zealand Re.: Application No. 556062.
Official Action Dated May 3, 2010 From the US Patent and Trademark Office Re.: U.S. Appl. No. 11/989,585.
Response Dated May 23, 2010 to Office Action of Jan. 22, 2010 From the State Intellectual Property Office of the People's Republic of China Re.: Application No. 200580047583.2.

* cited by examiner

PROCESS OF PREPARING BROMOPICRIN

RELATED APPLICATIONS

This Application is a National Phase of PCT Patent Application No. PCT/IL2006/000978 having International Filing Date of Aug. 22, 2006, which claims the benefit of U.S. Provisional Patent Application No. 60/711,272 filed on Aug. 26, 2005. The contents of the above Applications are all incorporated herein by reference.

FIELD AND BACKGROUND OF THE INVENTION

The present invention relates to the field of chemical synthesis and manufacturing, and more particularly, to a process of preparing bromopicrin, and high purity bromopicrin produced therefrom.

Bromopicrin, synonymously known as 1,1,1-tribromonitromethane (methane, tribromonitro-), nitrotribromomethane (methane, nitrotribromo-), and nitrobromoform, has chemical formula of $CBr_3NO_2$, molecular formula of $Br_3CNO_2$, molecular weight of 297.728, melting point of 10° C., boiling point of 89-90° C. (at 20 mm Hg), specific gravity of 2.79, water solubility of about 1.5 grams per liter water at 20° C., and appears as prismatic crystals in the solid phase, or as an oily colorless liquid. Bromopicrin is assigned CAS (Chemical Abstract Service) Registry No. 464-10-8, Beilstein Handbook Reference No. 4-01-00-00106, and can be considered as belonging to the general chemical family of halonitroalkanes (or equivalently, nitrohaloalkanes), including, for example, mono-, di-, and tri-, bromonitroalkanes and mono-, di-, and tri-, chloronitroalkanes, such as mono-, di-, and tri-, bromonitromethanes and mono-, di-, and tri-, chloronitromethanes, respectively.

In general, bromonitromethanes, such as tribromonitromethane (bromopicrin) and monobromonitromethane, are known for being used alone as an 'end-product', or, in a composition or formulation end-product, or, as a 'consumable' initial or intermediate reactant or ingredient in a process of preparing (synthesizing or/and manufacturing) another composition or formulation. Such chemical substances and materials which contain, or are derived from, bromonitromethanes are well known and widely used as antimicrobial, biocide, or/and antiseptic, agents, in a variety of different fields, such as agriculture, horticulture, and general industry. Bromonitromethanes are known as being quite useful, effective, and relatively safe, in agricultural applications involving eradication or/and prevention of soil-borne agricultural pests, and in general industrial applications involving eradication or/and prevention of noxious microorganisms. In particular, regarding commercial applicability, where worker and environmental health and safety considerations are major factors, bromonitromethanes and uses thereof have been developed as viable, effective, and safe, replacements or alternatives of effective, but environmentally problematic chemicals, such as methyl bromide, 1,3-dichloropropene, methyl isothiocyanates, methyl iodide (iodomethane), propargyl bromide, among others.

Uses of Bromopicrin and Related Bromonitromethanes:

Selected examples of bromonitromethanes, such as bromopicrin, which are indicated as possibly being used alone as an end-product, or, in a composition or formulation end-product, are provided in the disclosures of recently filed U.S. Prov. Patent Application No. 60/634,525, filed Dec. 10, 2004, by the same applicant/assignee of the present invention; U.S. Pat. No. 5,866,511, to Dallmier, et al.; U.S. Pat. No. 5,591, 759, to Ito, et al., U.S. Pat. Nos. 5,411,990, and 5,397,804, each to Tsuji, et al.; U.S. Pat. No. 5,013,762, to Smith, et al.; and U.S. Pat. Nos. 4,039,731; 4,020,249; 4,017,666; and 3,968,096, each to Freedman, et al.

In recently filed U.S. Prov. Patent Application No. 60/634, 525, there are disclosed methods, formulations, and articles of manufacturing utilizing formulations comprising bromopicrin or analogs thereof for effectively, reliably, and safely, disinfecting substances, products or structures and/or controlling plant pests, such as fungi, bacteria, insects, or weeds.

In U.S. Pat. No. 5,866,511, there is disclosed a method of inhibiting microbial growth in aqueous media, comprising adding to a microbe-containing aqueous media an acidified solution of (mono) bromonitromethane $[CH_2BrNO_2]$ in an amount sufficient to inhibit the growth of microbes (bacteria, algae, fungi) in the media.

In U.S. Pat. No. 5,591,759, there is disclosed an aqueous isothiazolone formulation useful for antiseptic or antifungal treatment of various synthetic polymeric emulsions, which comprises (a) a specific isothiazolone compound, (b) water or an aqueous solvent and (c) a specific nitrobromo compound, for example, tribromonitromethane (bromopicrin), or a cyanobromo compound.

In U.S. Pat. Nos. 5,411,990, and 5,397,804, there are disclosed industrial microbicidal or microbistatic agents, and corresponding methods of using thereof, for killing microbes or inhibiting the growth of microbes for industrial use which is effective for antiseptic, microbiocidal or microbiostatic treatment of a wide variety of different media and substances, such as water used in the paper manufacturing steps in paper and pulp industries; water for cooling and for washing in various industries; fuel oil sludge; metal working fluid; textile oil; paint; antifouling paint; coating color for paper; latex; and adhesives. In U.S. Pat. No. 5,411,990, an exemplary specific preferred embodiment of the disclosed industrial microbicidal comprises at least one haloglyoxime derivative, at least one known industrial microbiocidal ingredient, such as an organohalogen compound, for example, an organic bromonitro compound, for example, tribromonitromethane (bromopicrin), as an effective ingredient, and optionally a carrier or diluent. In U.S. Pat. No. 5,397,804, an exemplary specific preferred embodiment of the disclosed industrial microbicidal comprises chlorobenzaldoxime as an active ingredient, and a known industrial microbiocidal ingredient, such as an organobromine compound, for example, tribromonitromethane (bromopicrin).

In U.S. Pat. No. 5,013,762, there is disclosed a method for the treatment of nematodes (worm-like organisms found in soil) by applying to the soil a composition including a nematicidal amount of monobromonitromethane.

In U.S. Pat. Nos. 4,039,731; 4,020,249; 4,017,666; and 3,968,096, there are disclosed photodegradable (plastic) compositions comprising a polyolefin and about from 0.1 to 10 percent, based on the weight of the polyolefin, of an additive, for example, which contains bromine and a nitrogen group, for example, a halonitroalkane, such as tribromonitromethane (bromopicrin).

It is worthy to note that in each of the above disclosures, the bromonitromethane, that is, monobromonitromethane or tribromonitromethane (bromopicrin), is not synthesized or manufactured therein, but, rather obtained and used as a readily available stock reagent. It is additionally worthy to note that, except in the same applicant/assignee U.S. Prov. Patent Application No. 60/634,525, wherein the bromopicrin used is of analytical grade, in none of the other cited prior art is there any mention of the purity or source of the tribromonitromethane (bromopicrin).

Selected examples of tribromonitromethane (bromopicrin) [$CBr_3NO_2$] indicated as possibly being used as a consumable reactant or ingredient in processes of preparing another composition or formulation are provided in the disclosures of U.S. Pat. Nos. 5,219,938, and 5,128,416, each to Imai, et al., entitled: "Modified Diene Polymer Rubbers"; and U.S. Pat. Nos. 5,015,692, and 4,957,976, each to Takao, et al., entitled: "Process For Preparing Diene Polymer Rubbers".

It is worthy to note that, except in U.S. Pat. No. 4,922,030, wherein monobromonitromethane is custom synthesized for subsequent use in the disclosed process of preparing a composition or formulation of a monobromonitroalcohol, in each of the above disclosures, the bromonitromethane is not synthesized therein, but, rather obtained and used as a readily available stock reagent. It is additionally worthy to note that in none of the cited prior art is there any mention of the purity or source of the tribromonitromethane (bromopicrin).

Preparing Monobromonitromethane:

In general, methods or processes of synthesizing or/and manufacturing halonitroalkanes (nitrohaloalkanes) are well known and described, for example, in Tscherniak, in Ann. 180, 128-130 (1876); U.S. Pat. No. 2,309,806, to Tindall; U.S. Pat. No. 2,633,776, to Slagh; U.S. Pat. No. 4,922,030, to Nocito, et al.; U.S. Pat. No. 5,043,489, to Nocito, et al.; and U.S. Pat. No. 5,180,859, to Timberlake, et al.

Since bromopicrin (tribromonitromethane) is in the same general group, that is, bromonitroalkanes, as monobromonitromethane, as exemplary halonitroalkanes, one may expect that prior art teachings of methods of preparing monobromonitromethane either anticipate, or/and are obviously applicable to, methods of preparing bromopicrin. By reviewing the above-cited prior art teachings of methods or processes of preparing monobromonitromethane, as a well known and widely used bromonitroalkane, clearly this is not the case. As a matter of fact, it turns out that in the immediately following cited disclosures of methods or processes of preparing monobromonitromethane, the reaction products bromopicrin (tribromonitromethane) and dibromonitromethane are described as being formed only in the context as undesirable polyhalogenated nitromethane low yield by-products or impurities of the desired monobromonitromethane product. In none of the below disclosures is there description of a process or procedure for preparing pure bromopicrin as the target product in high yield.

As previously stated hereinabove, in the above disclosures of methods or processes of preparing monobromonitromethane, the reaction products bromopicrin (tribromonitromethane) and dibromonitromethane are described as being formed only in the context as undesirable polyhalogenated nitromethane low yield by-products or impurities of the desired monobromonitromethane product. In none of the above disclosures is there description of a process or procedure of preparing pure bromopicrin as the target product in high yield.

Preparing Bromopicrin (Tribromonitromethane):

Preparation of Bromopicrin by the Distillation of an Aqueous Mixture of Picric Acid, calcium hydroxide, and bromine, was first disclosed by Stenhouse, in Annalen 91, 307 (1854). It is also known from prior art teachings that bromopicrin can be prepared by reaction of picric acid with a basic metal hypobromite, and isolating the bromopicrin product in high yield by distillation.

The preceding prior art methods or processes of preparing bromopicrin have several significant disadvantages and limitations with regard to preparing pure bromopicrin in high yield in a manner which is industrially applicable, reproducible, safe, environmentally friendly, and cost effective. First, picric acid is potentially explosive under not such extreme conditions, and therefore, using picric acid as a reactant involves working at potentially hazardous conditions. Second, aside from picric acid, bromopicrin is a relatively highly energetic compound (that is, bromopicrin has a relatively high exothermic heat of decomposition (HOD), whereby about 1700 Joules/gram are released during its decomposition) and is potentially hazardous under certain conditions, and therefore, recovering and purifying bromopicrin from a reaction mixture by distillation, also involves working at potentially hazardous conditions. Third, in the event that solvent extraction is used instead of distillation for recovering and purifying bromopicrin from the reaction product, then an extraction procedure, including use and disposal of an appropriate organic solvent, for example, methylene chloride, needs to be incorporated into the overall process. However, such incorporation introduces an organic solvent into an otherwise organic solvent-free process, which would add additional costs, health hazards, and organic solvent waste management, to the overall process. Fourth, aside from the potential explosive and health hazards associated with obtaining high yields of pure bromopicrin via distillation or extraction, there is the factor of cost effectiveness in scaling up such recovery and purification methods to a large volume industrial sized process. For obtaining high yields of pure bromopicrin, there would probably be a need for relatively expensive distillation or extraction equipment, along with the costs involved for operating and maintaining thereof.

As previously stated hereinabove, in the disclosure of recently filed U.S. Prov. Patent Application No. 60/634,525, by the same applicant/assignee of the present invention, there are disclosed novel methods, formulations, and articles of manufacturing, utilizing formulations comprising bromopicrin or analogs thereof for effectively, reliably, and safely, disinfecting substances, products or structures or/and controlling plant pests, such as fungi, bacteria, insects, or weeds.

Based on potentially new wide commercial use and application of bromopicrin as an effective and relatively safe antimicrobial, biocide, or/and antiseptic, agent, in a variety of different fields, such as agriculture, horticulture, and general industry, there is a significant need for having industrially applicable, reproducible, safe, environmentally friendly, and cost effective, methods or processes of preparing high purity bromopicrin.

In view of the above significant disadvantages and limitations associated with prior art methods or processes of preparing high purity bromopicrin in high yields on an industrial scale, there is thus a need for developing improved or/and new methods or processes of preparing high purity bromopicrin, especially in high yields. There is a particular need for such an invention which includes an industrially applicable, reproducible, safe, environmentally friendly, and cost effective, procedure for collecting the high purity bromopicrin produced therefrom. Moreover, there is also a need for such an invention which provides bromopicrin having a purity equal to or greater than 96 weight percent, and as high as 99 percent.

SUMMARY OF THE INVENTION

The present invention relates to a process of preparing bromopicrin, and high purity bromopicrin produced therefrom. The process of the present invention is based on adding an aqueous solution of an alkaline substance, for example, a metal alkali base, such as sodium hydroxide, to a mixture of nitromethane and bromine, preferably, which is absent of an organic solvent, and collecting the organic phase containing the bromopicrin directly, in particular, via gravity (e.g., by free or forced draining or pumping), from the reaction mixture, without subjecting the organic phase to distillation or extraction, for obtaining near quantitative (theoretical stoichiometric) yield of bromopicrin having a purity equal to or greater than 96 percent, and as high as 99 weight percent (weight bromopicrin/total weight of the organic phase).

The process of preparing bromopicrin, of the present invention, includes the following main procedures: (a) providing a mixture of nitromethane and bromine, (b) subsequent to providing the mixture, adding an aqueous solution of an alkaline substance to the mixture, to thereby provide a reaction mixture containing the bromopicrin, the adding being performed such that no excess of the alkaline substance occurs in the reaction mixture during the adding of the aqueous solution, and (c) collecting the bromopicrin from the reaction mixture. The bromopicrin produced from the process of the present invention has a purity equal to or greater than 96 weight percent. Moreover, bromopicrin having a purity equal to or greater than 99 weight percent can be obtained by implementing the process of the present invention. The present invention is industrially applicable, reproducible, safe, environmentally friendly, and cost effective.

Selectivity of the reaction for producing bromopicrin is a function of several process parameters. Primary process parameters controlling selectivity of the reaction are: (1) the molar ratio of bromine and nitromethane used for providing the mixture of nitromethane and bromine (via procedure (a)), and (2) the temperature of the reaction (herein, also referred to as reaction temperature ($T_R$)) while bromopicrin is formed, corresponding to the temperature of the reaction mixture containing bromopicrin so formed, maintained throughout adding of the aqueous solution of the alkaline substance to the mixture of nitromethane and bromine, or, preferably, to the mixture of water, nitromethane, and bromine (via procedure (b)). Secondary process parameters are: (1) the concentration of the alkaline substance in the aqueous solution thereof (via procedure (b)), and (2) the duration of the reaction (herein, also referred to as reaction time), corresponding to the time period spanning from the beginning to the end of adding the aqueous solution of the alkaline substance to the mixture of nitromethane and bromine, or, preferably, to the mixture of water, nitromethane, and bromine (via procedure (b)).

The overall process of preparing bromopicrin, according to the present invention, is summarized by the following 'generalized' chemical equation [1] (aq.=aqueous):

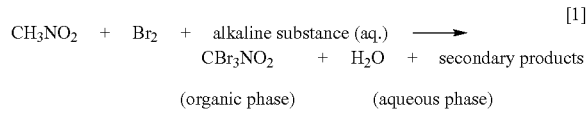

In procedure (a), providing the mixture of nitromethane and bromine is preferably performed without adding any organic solvent to the nitromethane and bromine, so that the mixture is substantially absent of an organic solvent. Preferably, procedure (a) is performed in a manner such that the mixture of nitromethane and bromine also includes water. In general, water is not needed in the mixture of nitromethane and bromine in order to commence the subsequent reaction between the nitromethane and the alkaline substance which is added to the mixture of nitromethane and bromine according to the next procedure, procedure (b). However, in procedure (a), preferably, water is included in the mixture of nitromethane and bromine, and mainly functions as a heat sink, by absorbing exothermic heat released during the subsequent reaction between the alkaline substance which is added in procedure (b) and the mixture of nitromethane and bromine.

In procedure (a), for providing the mixture of nitromethane and bromine, the most preferred order or sequence of mixing the nitromethane, bromine, and water, is that of adding nitromethane to water, for forming a mixture of water and nitromethane, followed by adding bromine to the mixture of water and nitromethane, for forming a mixture of water, nitromethane, and bromine.

In procedure (b), the alkaline substance is essentially any type of alkaline material which is capable of rapidly and selectively reacting with the bromine contained in the mixture of nitromethane and bromine (while in the presence of water and nitromethane), for forming one or more bromine-containing chemical intermediate(s), for example, a metal hypobromite formed by reaction between a metal alkali hydroxide, such as sodium hydroxide or potassium hydroxide and bromine, as generally indicated by chemical equation [2]:

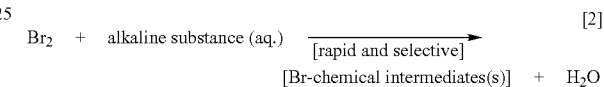

In turn, the one or more bromine-containing chemical intermediate(s), in the presence of water, selectively react(s) with the already present nitromethane, for selectively forming the desired high purity bromopicrin product in high (essentially, theoretical stoichiometric) yield, as generally indicated by chemical equation [3]:

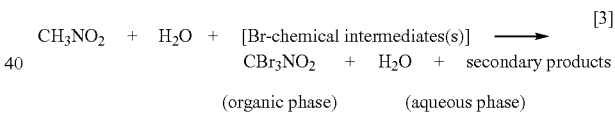

Procedure (b) is performed in a manner such that no excess of the alkaline substance occurs in the reaction mixture containing the bromopicrin, during the adding of the aqueous solution of the alkaline substance. Accordingly, absence of excess alkaline substance in the reaction mixture containing bromopicrin prevents any possible undesirable reaction between excess alkaline substance and the bromopicrin, thereby preventing formation of impurities, thereby maximizing the purity and yield of the bromopicrin.

For performing procedure (b) according to a batch mode type of operation, throughout the time period or duration of adding the aqueous solution of the alkaline substance to the mixture of nitromethane and bromine, preferably, the mixture of nitromethane and bromine, and consequently, the reaction mixture of water, nitromethane, bromine, alkaline substance, and formed bromopicrin, in the chemical reactor, are continuously mixed, for example, by stirring, in the chemical reactor, for example, by using an automatically controllable mechanical or electro-mechanical stirrer.

Mixing of the reaction mixture, in the chemical reactor, throughout the time period or duration of adding the aqueous solution of the alkaline substance to the mixture of nitromethane and bromine, maximizes contact, and therefore, reaction, between the alkaline substance and the mixture of nitromethane and bromine. Such mixing of the reaction mixture in the chemical reactor also helps to assure that no localized regions or points of the alkaline substance are formed in the chemical reactor, thereby, conforming with the important condition or limitation in procedure (b) that no excess of the alkaline substance occurs in the reaction mixture containing the bromopicrin, during the adding of the aqueous solution of the alkaline substance. Such mixing of the reaction mixture in the chemical reactor also helps to assure uniform heat distribution, throughout the volume of the chemical reactor, thereby providing a chemical environment in the chemical reactor for producing high purity bromopicrin in high (essentially, theoretical stoichiometric) yield.

In procedure (b), complete disappearance of the red to brown color of the reaction mixture of water, nitromethane, bromine, alkaline substance, and formed bromopicrin (being an oily colorless liquid at room temperature), accurately and precisely indicates completion of reaction of the alkaline substance with the bromine, and consequently with the nitromethane, in the reaction mixture, for forming high purity bromopicrin in high (essentially, theoretical stoichiometric) yield. This also corresponds to completion of the duration of the reaction (reaction time), at which time there is terminating the adding of the aqueous solution of the alkaline substance to the reaction mixture of water, nitromethane, bromine, alkaline substance, and formed bromopicrin.

Towards completion of procedure (b) in the overall process of preparing bromopicrin, the reaction mixture containing bromopicrin no longer includes meaningful quantities of bromine or alkaline substance. The bromine is no longer present in the reaction mixture since the bromine has completely reacted with (been consumed by) the alkaline substance, and consequently with the nitromethane, for forming bromopicrin. The compound in meaningful quantity contained in the heavier (lower) organic phase of the reaction mixture. Since the bromopicrin in the reaction mixture has a purity equal to or greater than 96 weight percent, and as high as 99 weight percent (weight bromopicrin/total weight of the organic phase), then, the heavier (lower) organic phase of the reaction mixture consists essentially only of bromopicrin. Therefore, performing procedure (c) of collecting the bromopicrin from the reaction mixture essentially corresponds to collecting the heavier (lower) organic phase (containing the bromopicrin) from the reaction mixture provided by procedure (b).

In procedure (c), the heavier (lower) organic phase (containing the bromopicrin) of the reaction mixture is directly collected from the reaction mixture. Preferably, the heavier (lower) organic phase containing the bromopicrin is directly collected via gravity, for example, by free or forced draining or pumping, from the reaction mixture.

The process of preparing bromopicrin of the present invention may include any number and types of optional additional procedures, depending at least partly on the actual operating conditions and process parameters used for implementing the process, and the results obtained therefrom, and depending upon the actual needs, requirements, and objectives, of a particular application involving implementation of the present invention.

For an exemplary preferred embodiment of the process of preparing bromopicrin, according to the present invention, wherein the alkaline substance is, for example, a metal alkali base, such as sodium hydroxide or potassium hydroxide, the overall process of preparing bromopicrin, according to the present invention, is summarized by the following chemical equations [4] and [5], for sodium hydroxide and potassium hydroxide, respectively:

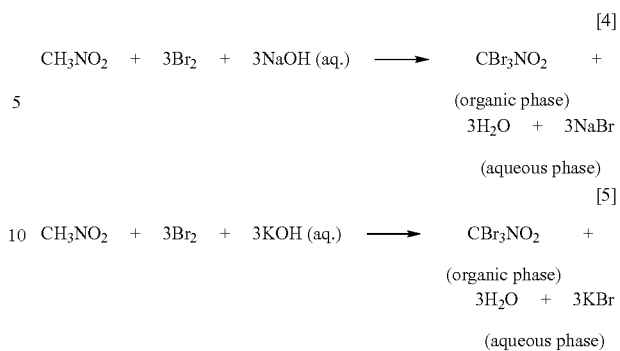

Thus, according to the present invention, there is provided a process of preparing bromopicrin, the process comprising: providing a mixture of nitromethane and bromine; subsequent to providing the mixture, adding an aqueous solution of an alkaline substance to the mixture, to thereby provide a reaction mixture containing the bromopicrin, the adding being performed such that no excess of the alkaline substance occurs in the reaction mixture during the adding of the aqueous solution; and collecting bromopicrin from the reaction mixture.

According to further characteristics in preferred embodiments of the invention described below, providing the mixture of the nitromethane and the bromine is performed such that the mixture is substantially absent of an organic solvent.

According to further characteristics in preferred embodiments of the invention described below, during providing the mixture of the nitromethane and the bromine, temperature of the mixture is in a range of between about 10° C. and about 50° C.

According to further characteristics in preferred embodiments of the invention described below, temperature of the mixture of nitromethane and bromine is in a range of between about 20° C. and about 25° C.

According to further characteristics in preferred embodiments of the invention described below, providing the mixture is performed using a molar ratio of bromine and nitromethane in a range of between about 3 and about 4.

According to further characteristics in preferred embodiments of the invention described below, providing the mixture is performed using a molar ratio of bromine and nitromethane in a range of between about 3 and about 3.5.

According to further characteristics in preferred embodiments of the invention described below, the mixture of the nitromethane and the bromine further includes water.

According to further characteristics in preferred embodiments of the invention described below, providing the mixture is performed according to a sequence of adding the alkaline substance is no longer present in the reaction mixture since the alkaline substance has completely reacted with the bromine, and consequently with the nitromethane, for forming bromopicrin. Addition of the aqueous solution of the alkaline substance to the reaction mixture was terminated, thus, precluding introduction of additional alkaline substance to the reaction mixture, thereby assuring absence of excess alkaline substance in the reaction mixture containing the bromopicrin. Both the bromine and the alkaline substance have completely reacted with each other, in the presence of water, for forming one or more bromine-containing chemical intermediate(s), as generally indicated by chemical equation [2]. In turn, the one or more bromine-containing chemical intermediate(s), in the presence of water, selectively react(s) with the already present nitromethane, for selectively forming high purity bromopicrin product in high (essentially, theoretical stoichiometric) yield, as generally indicated by chemical equation [3].

Thus, towards completion of procedure (b), the reaction mixture containing bromopicrin is characterized by including as primary products: bromopicrin [$CBr_3NO_2$] and water, and as secondary products: inorganic salt(s), in particular, bromide salt(s); inorganic oxidant(s), in particular, hypobromite, bromite, and bromate, oxidants; and trace quantities of organic or/and inorganic materials. Clearly the actual type and distribution of secondary products depends upon the actual type of alkaline substance included in the aqueous solution of the alkaline substance which is added to the mixture of nitromethane and bromine, and depends upon the actual operating conditions and process parameters used for performing procedures (a) and (b).

Mixing, via stirring, of the reaction mixture containing bromopicrin is terminated, and the reaction mixture is allowed to undergo phase separation and phase equilibrium. During phase separation and equilibrium, the primary product bromopicrin, having a water solubility of about 1.5 grams per liter water at 20° C., and a specific gravity of 2.79, migrates into and becomes the heavier (lower) organic phase, while the primary product water and the secondary products migrate into and become the lighter (upper) aqueous phase, of the reaction mixture. Accordingly, the two phases, that is, the heavier (lower) organic phase (containing bromopicrin) and the lighter (upper) aqueous phase (containing water and secondary products), of the reaction mixture, are allowed to separate from each other, and are allowed to reach phase equilibrium.

In accordance with the process of preparing bromopicrin of the present invention, by performing procedures (a) and (b), the bromopicrin so produced is the only organic nitromethane to the water, followed by adding the bromine to the nitromethane and the water, thereby forming the mixture.

According to further characteristics in preferred embodiments of the invention described below, providing the mixture is performed using a weight ratio of the nitromethane and the water in a range of between about 0.25 and about 4.

According to further characteristics in preferred embodiments of the invention described below, providing the mixture is performed using a weight ratio of the nitromethane and the water in a range of between about 0.5 and about 2.

According to further characteristics in preferred embodiments of the invention described below, the alkaline substance is selected from the group consisting of metal alkali hydroxides, alkaline earth hydroxides, and combinations thereof.

According to further characteristics in preferred embodiments of the invention described below, the metal alkali hydroxide is selected from the group consisting of lithium hydroxide, sodium hydroxide, potassium hydroxide, and a combination thereof.

According to further characteristics in preferred embodiments of the invention described below, the metal alkali hydroxide is selected from the group consisting of sodium hydroxide, potassium hydroxide, and a combination thereof.

According to further characteristics in preferred embodiments of the invention described below, the alkaline substance is sodium hydroxide.

According to further characteristics in preferred embodiments of the invention described below, the alkaline earth hydroxide is selected from the group consisting of magnesium hydroxide, calcium hydroxide, strontium hydroxide, and barium hydroxide.

According to further characteristics in preferred embodiments of the invention described below, concentration of the alkaline substance in the aqueous solution of the alkaline substance is in a range of between about 5 weight percent and about 50 weight percent (weight alkaline substance/weight aqueous solution).

According to further characteristics in preferred embodiments of the invention described below, concentration of the alkaline substance in the aqueous solution of the alkaline substance is in a range of between about 25 weight percent and about 40 weight percent (weight alkaline substance/weight aqueous solution).

According to further characteristics in preferred embodiments of the invention described below, concentration of the alkaline substance in the aqueous solution of the alkaline substance is about 35 weight percent (weight alkaline substance/weight aqueous solution).

According to further characteristics in preferred embodiments of the invention described below, prior to adding the aqueous solution to the mixture, temperature of the mixture is in a range of between about 10° C. and about 50° C.

According to further characteristics in preferred embodiments of the invention described below, temperature of the reaction mixture maintained throughout adding of the aqueous solution to the mixture is in a range of between about 20° C. and about 50° C.

According to further characteristics in preferred embodiments of the invention described below, temperature of the reaction mixture maintained throughout adding of the aqueous solution to the mixture is in a range of between about 35° C. and about 45° C.

According to further characteristics in preferred embodiments of the invention described below, adding the aqueous solution to the mixture is performed during a time period in a range of between about 0.5 hour and about 24 hours.

According to further characteristics in preferred embodiments of the invention described below, adding the aqueous solution to the mixture is performed during a time period in a range of between about 1 hour and about 10 hours.

According to further characteristics in preferred embodiments of the invention described below, adding the aqueous solution to the mixture is performed during a time period in a range of between about 2 hours and about 6 hours.

According to further characteristics in preferred embodiments of the invention described below, collecting the bromopicrin from the reaction mixture is performed by free or forced draining or pumping of organic phase from the reaction mixture.

According to further characteristics in preferred embodiments of the invention described below, following the collecting the bromopicrin, there is collecting aqueous phase from the reaction mixture and chemically treating the aqueous phase, thereby providing a treated form of the aqueous phase.

According to further characteristics in preferred embodiments of the invention described below, the treated form of the aqueous phase is used in a procedure for isolating sodium bromide, producing bromine, or producing hydrobromic acid.

According to further characteristics in preferred embodiments of the invention described below, there is provided bromopicrin prepared by the hereinabove process.

According to further characteristics in preferred embodiments of the invention described below, the bromopicrin has a purity equal to or greater than 96 weight percent (weight bromopicrin/total weight of organic phase of the reaction mixture).

According to further characteristics in preferred embodiments of the invention described below, the bromopicrin has a purity equal to or greater than 99 weight percent.

According to another aspect of the present invention, there is provided bromopicrin having a purity equal to or greater than 96 weight percent.

According to further characteristics in preferred embodiments of the invention described below, the bromopicrin purity is equal to or greater than 99 weight percent.

The present invention can be implemented by performing procedures, steps, and sub-steps, in a manner selected from the group consisting of manually, semi-automatically, fully automatically, and a combination thereof, involving use and operation of equipment and materials, in a manner selected from the group consisting of manually, semi-automatically, fully automatically, and a combination thereof. Moreover, according to actual procedures, steps, sub-steps, and, equipment and materials, used for implementing a particular embodiment of the disclosed invention, the procedures, steps, and sub-steps, are performed by using hardware, software, or/and an integrated combination thereof, and the equipment and materials operate by using hardware, software, or/and an integrated combination thereof.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

Figure 1:
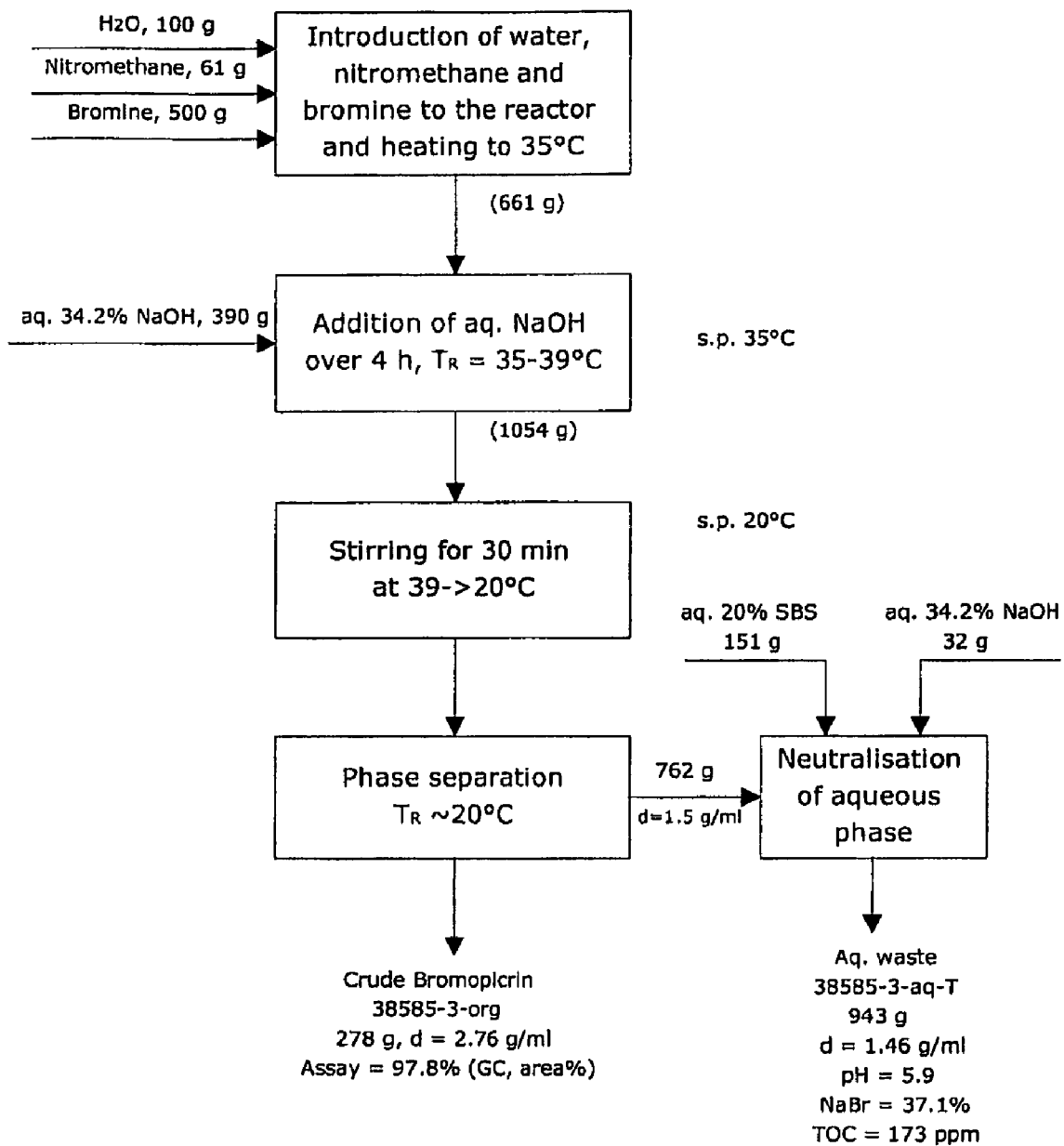
FIG. 1 is a flow block diagram of the actual scheme and procedures of an example of implementing the present invention on the laboratory scale, using a 1 liter size chemical reactor, for reaction conditions and results of an exemplary run, Run no. 38585-3, as described in the Examples, in accordance with the present invention.

The present invention relates to a process of preparing bromopicrin, and high purity bromopicrin produced therefrom. The process of the present invention is based on adding an aqueous solution of an alkaline substance, for example, a metal alkali base, such as sodium hydroxide, to a mixture of nitromethane and bromine, preferably which is absent of an organic solvent, and collecting the organic phase containing the bromopicrin directly, in particular, via gravity (e.g., by free or forced draining or pumping), from the reaction mixture, without subjecting the organic phase to distillation or extraction, for obtaining near quantitative (theoretical stoichiometric) yield of bromopicrin having a purity equal to or greater than 96 percent, and as high as 99 weight percent (weight bromopicrin/total weight of the organic phase).

The process of preparing bromopicrin, according to the present embodiments, includes the following main procedures: (a) providing a mixture of nitromethane and bromine, (b) subsequent to providing the mixture, adding an aqueous solution of an alkaline substance to the mixture, to thereby provide a reaction mixture containing the bromopicrin, the adding being performed such that no excess of the alkaline substance occurs in the reaction mixture during the adding of the aqueous solution, and (c) collecting the bromopicrin from the reaction mixture. The bromopicrin produced from the process of the present invention has a purity equal to or greater than 96 weight percent. Moreover, bromopicrin having a purity equal to or greater than 99 weight percent can be obtained by implementing the process of the present invention. The present invention is industrially applicable, reproducible, safe, environmentally friendly, and cost effective.

Selectivity of the reaction for producing bromopicrin is a function of several process parameters. Primary process parameters controlling selectivity of the reaction are: (1) the molar ratio of bromine and nitromethane used for providing the mixture of nitromethane and bromine (via procedure (a)), and (2) the temperature of the reaction (herein, also referred to as reaction temperature ($T_R$)) while bromopicrin is formed, corresponding to the temperature of the reaction mixture containing bromopicrin so formed, maintained throughout adding of the aqueous solution of the alkaline substance to the mixture of nitromethane and bromine, or, preferably, to the mixture of water, nitromethane, and bromine (via procedure (b)). Secondary process parameters are: (1) the concentration of the alkaline substance in the aqueous solution thereof (via procedure (b)), and (2) the duration of the reaction (herein, also referred to as reaction time), corresponding to the time period spanning from the beginning to the end of adding the aqueous solution of the alkaline substance to the mixture of nitromethane and bromine, or, preferably, to the mixture of water, nitromethane, and bromine (via procedure (b)).

The overall process of preparing bromopicrin, according to the present invention, is summarized by the following 'generalized' chemical equation [1] (aq.=aqueous):

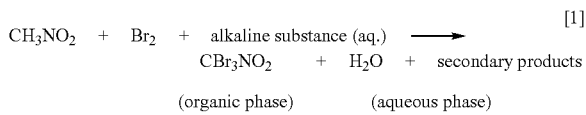

In procedure (a), providing the mixture of nitromethane and bromine is preferably performed without adding any organic solvent to the nitromethane and bromine, so that the mixture is substantially absent of an organic solvent. Preferably, procedure (a) is performed in a manner such that the mixture of nitromethane and bromine also includes water. In general, water is not needed in the mixture of nitromethane and bromine in order to commence the subsequent reaction between the nitromethane and the alkaline substance which is added to the mixture of nitromethane and bromine according to the next procedure, procedure (b). However, in procedure (a), preferably, water is included in the mixture of nitromethane and bromine, and mainly functions as a heat sink, by absorbing exothermic heat released during the subsequent reaction between the alkaline substance which is added in procedure (b) and the mixture of nitromethane and bromine.

In procedure (a), for providing the mixture of nitromethane and bromine, the most preferred order or sequence of mixing the nitromethane, bromine, and water, is that of adding nitromethane to water, for forming a mixture of water and nitromethane, followed by adding bromine to the mixture of water and nitromethane, for forming a mixture of water, nitromethane, and bromine.

In procedure (b), the alkaline substance is essentially any type of alkaline material which is capable of rapidly and selectively reacting with the bromine contained in the mixture of nitromethane and bromine (while in the presence of water and nitromethane), for forming one or more bromine-containing chemical intermediate(s), for example, a metal hypobromite formed by reaction between a metal alkali hydroxide, such as sodium hydroxide or potassium hydroxide and bromine, as generally indicated by chemical equation [2]:

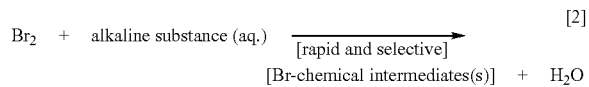

In turn, the one or more bromine-containing chemical intermediate(s), in the presence of water, selectively react(s) with the already present nitromethane, for selectively forming the desired high purity bromopicrin product in high (essentially, theoretical stoichiometric) yield, as generally indicated by chemical equation [3]:

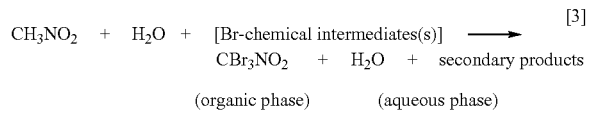

Procedure (b) is performed in a manner such that no excess of the alkaline substance occurs in the reaction mixture containing the bromopicrin, during the adding of the aqueous solution of the alkaline substance. Accordingly, absence of excess alkaline substance in the reaction mixture containing bromopicrin prevents any possible undesirable reaction between excess alkaline substance and the bromopicrin, thereby preventing formation of impurities, thereby maximizing the purity and yield of the bromopicrin.

For performing procedure (b) according to a batch mode type of operation, throughout the time period or duration of adding the aqueous solution of the alkaline substance to the mixture of nitromethane and bromine, preferably, the mixture of nitromethane and bromine, and consequently, the reaction mixture of water, nitromethane, bromine, alkaline substance, and formed bromopicrin, in the chemical reactor, are continuously mixed, for example, by stirring, in the chemical reactor, for example, by using an automatically controllable mechanical or electro-mechanical stirrer.

Mixing of the reaction mixture, in the chemical reactor, throughout the time period or duration of adding the aqueous solution of the alkaline substance to the mixture of nitromethane and bromine, maximizes contact, and therefore, reaction, between the alkaline substance and the mixture of nitromethane and bromine. Such mixing of the reaction mixture in the chemical reactor also helps to assure that no localized regions or points of the alkaline substance are formed in the chemical reactor, thereby, conforming with the important condition or limitation in procedure (b) that no excess of the alkaline substance occurs in the reaction mixture containing the bromopicrin, during the adding of the aqueous solution of the alkaline substance. Such mixing of the reaction mixture in the chemical reactor also helps to assure uniform heat distribution, throughout the volume of the chemical reactor, thereby providing a chemical environment in the chemical reactor for producing high purity bromopicrin in high (essentially, theoretical stoichiometric) yield.

In procedure (b), complete disappearance of the red to brown color of the reaction mixture of water, nitromethane, bromine, alkaline substance, and formed bromopicrin (being an oily colorless liquid at room temperature), accurately and precisely indicates completion of reaction of the alkaline substance with the bromine, and consequently with the nitromethane, in the reaction mixture, for forming high purity bromopicrin in high (essentially, theoretical stoichiometric) yield. This also corresponds to completion of the duration of the reaction (reaction time), at which time there is terminating the adding of the aqueous solution of the alkaline substance to the reaction mixture of water, nitromethane, bromine, alkaline substance, and formed bromopicrin.

Towards completion of procedure (b) in the overall process of preparing bromopicrin, the reaction mixture containing bromopicrin no longer includes meaningful quantities of bromine or alkaline substance. The bromine is no longer present in the reaction mixture since the bromine has completely reacted with (been consumed by) the alkaline substance, and consequently with the nitromethane, for forming bromopicrin. The alkaline substance is no longer present in the reaction mixture since the alkaline substance has completely reacted with the bromine, and consequently with the nitromethane, for forming bromopicrin. Addition of the aqueous solution of the alkaline substance to the reaction mixture was terminated, thus, precluding introduction of additional alkaline substance to the reaction mixture, thereby assuring absence of excess alkaline substance in the reaction mixture containing the bromopicrin. Both the bromine and the alkaline substance have completely reacted with each other, in the presence of water, for forming one or more bromine-containing chemical intermediate(s), as generally indicated by chemical equation [2]. In turn, the one or more bromine-containing chemical intermediate(s), in the presence of water, selectively react(s) with the already present nitromethane, for selectively forming high purity bromopicrin product in high (essentially, theoretical stoichiometric) yield, as generally indicated by chemical equation [3].

Thus, towards completion of procedure (b), the reaction mixture containing bromopicrin is characterized by including as primary products: bromopicrin [$CBr_3NO_2$] and water, and as secondary products: inorganic salt(s), in particular, bromide salt(s); inorganic oxidant(s), in particular, hypobromite, bromite, and bromate, oxidants; and trace quantities of organic or/and inorganic materials. Clearly the actual type and distribution of secondary products depends upon the actual type of alkaline substance included in the aqueous solution of the alkaline substance which is added to the mixture of nitromethane and bromine, and depends upon the actual operating conditions and process parameters used for performing procedures (a) and (b).

Mixing, via stirring, of the reaction mixture containing bromopicrin is terminated, and the reaction mixture is allowed to undergo phase separation and phase equilibrium. During phase separation and equilibrium, the primary product bromopicrin, having a water solubility of about 1.5 grams per liter water at 20° C., and a specific gravity of 2.79, migrates into and becomes the heavier (lower) organic phase, while the primary product water and the secondary products migrate into and become the lighter (upper) aqueous phase, of the reaction mixture. Accordingly, the two phases, that is, the heavier (lower) organic phase (containing bromopicrin) and the lighter (upper) aqueous phase (containing water and secondary products), of the reaction mixture, are allowed to separate from each other, and are allowed to reach phase equilibrium.

In accordance with the process of preparing bromopicrin of the present invention, by performing procedures (a) and (b), the bromopicrin so produced is the only organic compound in meaningful quantity contained in the heavier (lower) organic phase of the reaction mixture. Since the bromopicrin in the reaction mixture has a purity equal to or greater than 96 weight percent, and as high as 99 weight percent (weight bromopicrin/total weight of the organic phase), then, the heavier (lower) organic phase of the reaction mixture consists essentially only of bromopicrin. Therefore, performing procedure (c) of collecting the bromopicrin from the reaction mixture essentially corresponds to collecting the heavier (lower) organic phase (containing the bromopicrin) from the reaction mixture provided by procedure (b).

In procedure (c), the heavier (lower) organic phase (containing the bromopicrin) of the reaction mixture is directly collected from the reaction mixture. Preferably, the heavier (lower) organic phase containing the bromopicrin is directly collected via gravity, for example, by free or forced draining or pumping, from the reaction mixture.

The process of preparing bromopicrin of the present invention may include any number and types of optional additional procedures, depending at least partly on the actual operating conditions and process parameters used for implementing the process, and the results obtained therefrom, and depending upon the actual needs, requirements, and objectives, of a particular application involving implementation of the present invention.

For an exemplary preferred embodiment of the process of preparing bromopicrin, according to the present invention, wherein the alkaline substance is, for example, a metal alkali base, such as sodium hydroxide or potassium hydroxide, the overall process of preparing bromopicrin, according to the present invention, is summarized by the following chemical equations [4] and [5], for sodium hydroxide and potassium hydroxide, respectively:

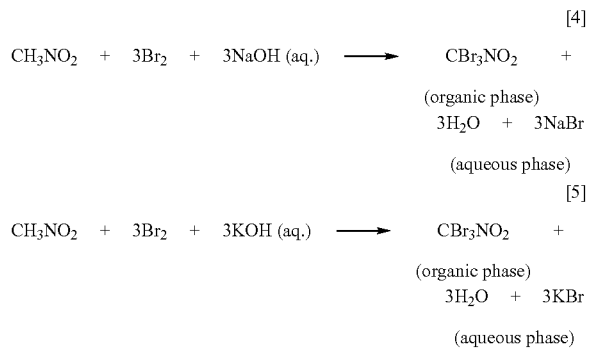

Details of exemplary implementation of the process of preparing bromopicrin, according to the present invention, wherein the alkaline substance is a metal alkali hydroxide, for example, sodium hydroxide or potassium hydroxide, as indicated by chemical equations [4] and [5], respectively, are provided in the Examples section, hereinbelow, following the Description section.

The present invention features several aspects of novelty and inventiveness, a few of which are indicated hereinbelow.

A main aspect of novelty and inventiveness of the present invention is that the process results in obtaining near quantitative (theoretical stoichiometric) yield of bromopicrin having a purity equal to or greater than 96 percent, and as high as 99 weight percent (weight bromopicrin/total weight of the organic phase).

Another main aspect of novelty and inventiveness of the present invention is that the process includes an industrially applicable, reproducible, safe, environmentally friendly, and cost effective, procedure for collecting the high purity bromopicrin produced therefrom. The organic phase containing the bromopicrin is directly collected, in particular, via gravity (e.g., by free or forced draining or pumping), from the reaction mixture, without subjecting the organic phase to distillation or extraction, for obtaining near quantitative (theoretical stoichiometric) yield of bromopicrin having a purity equal to or greater than 96 weight percent, and as high as 99 weight percent. This aspect results in precluding the need for including a distillation or extraction procedure along with relatively expensive distillation or extraction equipment, as well as costs involved for operating and maintaining thereof. This aspect also results in precluding the need for handling and taking into account the affects, in particular, as relating to health and safety, of the potentially hazardous (highly energetic) bromopicrin product during distillation or extraction conditions, as well as of the potentially hazardous and waste generating extraction solvent.

Another main aspect of novelty and inventiveness of the present invention is the preferred absence of an organic solvent throughout the entire process of preparing the bromopicrin. Accordingly, preferably, there is no organic solvent in the initial mixture of nitromethane and bromine, or in the subsequent reaction mixture containing the bromopicrin formed therefrom. This aspect results in precluding the possibility of introducing impurities or/and undesirable reaction intermediates and by-products into the process due to the presence of an organic solvent, and precluding the need for handling and taking into account the affects, in particular, as relating to health and safety, of using an organic solvent during any stage of the process of preparing the bromopicrin.

It is to be understood that the present invention is not limited in its application to the details of the order or sequence, and number, of procedures, steps, and sub-steps, of operation or implementation of the process, or to the details of the equipment, reagents, and materials, used for implementing the process, set forth in the following illustrative description, accompanying drawings, and examples, unless otherwise specifically stated herein. The present invention is capable of other embodiments and of being practiced or carried out in various ways. Although procedures, steps, sub-steps, equipment, reagents, and materials, similar or equivalent to those illustratively described herein can be used for practicing or testing the present invention, suitable procedures, steps, sub-steps, equipment, reagents, and materials, are illustratively described herein.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting. Moreover, all technical and scientific words, terms, or/and phrases, introduced, defined, described, or/and exemplified, in the above Background section, for example, regarding the synonyms of bromopicrin, are equally or similarly applicable in the illustrative description of the preferred embodiments, examples, and appended claims, of the present invention.

As used herein, the term 'about' refers to ±10 percent of the associated value. Additionally, as used herein, the phrase 'room temperature' refers to a temperature in a range of between about 20° C. and about 25° C.

Procedures, steps, sub-steps, equipment, reagents, and materials, and implementation, of exemplary preferred embodiments, alternative preferred embodiments, specific configurations, and, additional and optional aspects, characteristics, or features, thereof, of the process of preparing bromopicrin, and high purity bromopicrin produced therefrom, according to the present invention, are better understood with reference to the following illustrative description and accompanying drawings. Throughout the following illustrative description and accompanying drawings, same reference numbers, or/and letters, refer to same components.

In the following illustrative description of the process of the present invention, included are main or principal procedures, steps, sub-steps, equipment, reagents, and materials, needed for sufficiently understanding proper 'enabling' utilization and implementation of the disclosed process. Accordingly, description of various possible required or/and optional preliminary, intermediate, minor, procedures, steps, sub-steps, equipment, reagents, or/and materials, of secondary importance with respect to enabling implementation of the invention, which are readily known by one of ordinary skill in the art, or/and which are available in the prior art and technical literature relating to chemical synthesis and manufacturing, are at most only briefly indicated herein.

Thus, according to a main aspect of the present invention, there is provision of a process of preparing bromopicrin which includes the following main procedures: (a) providing a mixture of nitromethane and bromine, the mixture being substantially absent of an organic solvent, (b) adding an aqueous solution of an alkaline substance to the mixture, to thereby provide a reaction mixture containing the bromopicrin, the adding being performed such that no excess of the alkaline substance occurs in the reaction mixture during the adding of the aqueous solution, and (c) collecting the bromopicrin from the reaction mixture.

Detailed description of performing each main procedure (a), (b), and (c), as part of describing exemplary preferred implementation of the process of preparing bromopicrin, of the present invention, immediately follows hereinbelow. The process of preparing bromopicrin, and implementation thereof, according to the present invention, are generally described, and particularly described in the context of an exemplary batch mode type of operation of a chemical reaction process.

(a) Providing a Mixture of Nitromethane and Bromine:

For performing procedure (a) of providing a mixture of nitromethane and bromine, a quantity of nitromethane [chemical formula: $CH_3NO_2$; molecular weight: 61.0 grams/mole; density: 1.137 grams/ml; melting point: −29° C.; boiling point: 101.2° C.; water solubility: 9.5 grams/100 ml] and a quantity of bromine [chemical formula: $Br_2$; molecular weight: 159.8 grams/mole; density: 3.119 grams/ml; melting point: −7.2° C.; boiling point: 58.7° C.; water solubility: 3.5 grams/100 ml] are mixed. For performing this procedure according to a batch mode type of operation, a quantity of nitromethane [$CH_3NO_2$] and a quantity of bromine [$Br_2$] are each added to a batch mode type of chemical reactor, hereinafter, more briefly referred to as 'the chemical reactor'.

In procedure (a), in general, providing the mixture of nitromethane and bromine is performed with or without adding any organic solvent to the nitromethane and bromine. Preferably, procedure (a) is performed without adding any organic solvent to the nitromethane and bromine, so that the mixture is substantially absent of an organic solvent. Accordingly, in procedure (a), preferably, there is no organic solvent in the initial mixture of nitromethane and bromine, or in the subsequent reaction mixture containing the bromopicrin formed by the next procedure, procedure (b). This aspect of the present invention results in precluding the possibility of introducing impurities or/and undesirable reaction intermediates and by-products into the process due to the presence of an organic solvent, and precluding the need for handling and taking into account the affects, in particular, as relating to health and safety, of using an organic solvent during any stage of the process of preparing the bromopicrin.

Preferably, procedure (a) is performed in a manner such that the mixture of nitromethane and bromine also includes water. In general, water is not needed in the mixture of nitromethane and bromine in order to commence the subsequent reaction between the nitromethane and the alkaline substance which is added to the mixture of nitromethane and bromine according to the next procedure, procedure (b). However, in procedure (a), preferably; water is included in the mixture of nitromethane and bromine, wherein the water has two main functions. The first main function relates to the potential hazard of having a chemical reactor filled with a large volume of a liquid phase organic material, such as nitromethane, absent of water. The second main function relates to water serving as a heat sink, by absorbing exothermic heat released during the subsequent reaction between the alkaline substance which is added in procedure (b) and the mixture of nitromethane and bromine. Thus, preferably, procedure (a) of providing a mixture of nitromethane and bromine results in providing a mixture of water, nitromethane, and bromine, wherein the resulting mixture is substantially absent of an organic solvent.

For the preferred embodiment of the process of the present invention wherein water is included in the mixture of nitromethane and bromine, then, in general, procedure (a) of providing a mixture of nitromethane and bromine is performed in a manner such that the order or sequence of mixing the nitromethane, bromine, and water, can be varied. The most preferred order or sequence is that of adding nitromethane to water, for forming a mixture of water and nitromethane, followed by adding bromine to the mixture of water and nitromethane, for forming a mixture of water, nitromethane, and bromine. Clearly, alternative orders or sequences of mixing these reagents with each other are possible, for providing the mixture of nitromethane and bromine. For performing procedure (a) according to a batch mode type of operation, the preferred order or sequence of adding these reagents to the chemical reactor is: water, nitromethane, bromine. Clearly, alternative orders or sequences of adding these reagents to the chemical reactor are possible, for forming a mixture of water, nitromethane, and bromine, in the chemical reactor.

In general, the (initial) temperature of the mixture of nitromethane and bromine, (absent of water, or including water), can be varied. In general, the (initial) temperature of the mixture of nitromethane and bromine, (absent of water, or including water), is in a range of, preferably, between about 10° C. and about 50° C., and more preferably, between about 20° C. and about 25° C. (corresponding to room temperature).

Preferably, procedure (a) of providing a mixture of nitromethane and bromine is performed in a manner such that the water, nitromethane, and bromine, are each initially in the liquid phase, and remain in the liquid phase during formation of the mixture of water, nitromethane, and bromine. Accordingly, preferably, the water, nitromethane, and bromine, are each initially, and remain, at a temperature in a range bounded by their respective melting and boiling points, during formation of the mixture of water, nitromethane, and bromine. More preferably, the water, nitromethane, and bromine, are each initially, and remain, at room temperature (between about 20° C. and about 25° C.), during formation of the mixture of water, nitromethane, and bromine.

For performing procedure (a) according to a batch mode type of operation, accordingly, preferably, the water, nitromethane, and bromine, are each initially, and remain, at a temperature in a range bounded by their respective melting and boiling points, when added to the chemical reactor, and remain in the liquid phase during formation of the mixture of water, nitromethane, and bromine, in the chemical reactor. Accordingly, preferably, the water, nitromethane, and bromine, are each initially, and remain, at a temperature in a range bounded by their respective melting and boiling points, during formation of the mixture of water, nitromethane, and bromine. More preferably, the water, nitromethane, and bromine, are each initially, and remain, at room temperature (between about 20° C. and about 25° C.), when added to the chemical reactor, and during formation of the mixture of water, nitromethane, and bromine, in the chemical reactor.

As further described and exemplified hereinbelow, the molar ratio of bromine and nitromethane used for providing the mixture of nitromethane and bromine, is a primary process parameter for determining selectivity of the reaction for producing bromopicrin. At this stage of the overall process of preparing bromopicrin, an important objective is to create a chemical environment in the mixture of nitromethane and bromine, whereby, the molar ratio of bromine and nitromethane is sufficiently higher than one, such that upon commencement of the next procedure (that is, procedure (b)) of adding an aqueous solution of an alkaline substance to the mixture of nitromethane and bromine, the alkaline substance immediately and selectively reacts with the bromine, as indicated by chemical equation [2], above.

Procedure (a) of providing a mixture of nitromethane and bromine is performed by using a molar ratio of bromine and nitromethane in a unique empirically determined relatively narrow optimum range. The molar ratio of bromine and nitromethane used for providing the mixture is in a range of, preferably, between about 3 and about 4, more preferably, between about 3 and about 3.5. The optimum molar ratio of bromine and nitromethane used for providing the mixture is about 3.15.

For example, for an exemplary embodiment of the process of the present invention, wherein the alkaline substance is a metal alkali hydroxide, such as sodium hydroxide or potassium hydroxide, as indicated by chemical equations [4] and [5], respectively, the molar ratio of bromine and nitromethane used for providing the mixture of nitromethane and bromine is to be sufficiently higher than one, for example, about 3, such that upon commencement of the next procedure of adding an aqueous solution of the metal alkali hydroxide (sodium hydroxide or potassium hydroxide), to the mixture of nitromethane and bromine, the metal alkali hydroxide (sodium hydroxide or potassium hydroxide) immediately and selectively reacts with the bromine, for selectively forming the metal alkali hypobromite (sodium hypobromite [NaBrO] or potassium hypobromite [KBrO], respectively), as generally indicated by chemical equation [2], hereinabove, and further described and exemplified hereinbelow.

For the preferred embodiment of the process of the present invention wherein water is included in the mixture of nitromethane and bromine, then, performing procedure (a) includes using a quantity of water characterized by a concentration. The concentration of water may be expressed in terms, for example, of a weight ratio of nitromethane and water, corresponding to the ratio of the weight of nitromethane and the weight of water used for providing the mixture of nitromethane and bromine, when including water.

In general, the weight ratio of nitromethane and water used for providing the mixture of nitromethane and bromine, when including water, can be varied. The weight ratio of nitromethane and water used for providing the mixture of nitromethane and bromine, when including water, is in a range of, preferably, between about 0.25 and about 4, and more preferably, between about 0.5 and about 2.

For performing procedure (a) according to a batch mode type of operation, in general, the (initial) temperature of the chemical reactor used for providing the mixture of nitromethane and bromine can be varied. The (initial) temperature of the chemical reactor used for providing the mixture of nitromethane and bromine is in a range of, preferably, between about 10° C. and about 50° C., and more preferably, between about 20° C. and about 25° C. (corresponding to room temperature).

For performing procedure (a) according to a batch mode type of operation, preferably, during and following adding water, nitromethane, and bromine, to the chemical reactor, the added water, nitromethane, and bromine, are continuously mixed, for example, by stirring, in the chemical reactor. In this manner, the continuously mixed or stirred water, nitromethane, and bromine, form a uniform or homogeneous liquid phase mixture throughout the volume of the chemical reactor.

In general, essentially any batch mode type of chemical reactor can be used as the chemical reactor for performing procedure (a) of providing a mixture of nitromethane and bromine. Preferably, the chemical reactor is operatively constructed or fitted with equipment, for example, a temperature controllable chemical reactor jacket, for enabling manual, semi-automatic, or fully automatic, temperature control of the contents inside the chemical reactor, for pre-determined ranges of temperature, for example, with capability of setting the temperature inside the chemical reactor within an overall range of between about 10° C. and 50° C. In such an embodiment, preferably, the temperature controllable equipment is operatively connected to a manual, semi-automatic, or fully automatic, respectively, temperature controller, for example, a Lauda automatic chemical reactor temperature controller device operative with variable chemical reactor temperature set point, which, in turn, is operatively connected to an appropriate power supply. Additionally, preferably, the chemical reactor is operatively constructed or fitted with equipment, for example, a mechanical or electro-mechanical stirrer, for enabling manual, semi-automatic, or fully automatic, mixing or stirring control of the contents of the chemical reactor, for pre-determined ranges of mixing or stirring speed, and for pre-determined patterns or configurations of mixing or stirring. In such an embodiment, preferably, the mixing or stirring controllable equipment is operatively connected to a manual, semi-automatic, or fully automatic, respectively, mixing or stirring controller, which, in turn, is operatively connected to an appropriate power supply.

The mixture of nitromethane and bromine, (absent of water, or including water), thus formed and provided by procedure (a), is essentially a non-reactive mixture of two liquid phase compounds (without water) or three liquid phase compounds (with water).

The mixture of nitromethane and bromine, (absent of water, or including water), thus formed and provided by procedure (a), takes on a red to brown color, due to the red to brown color of liquid bromine, along with the water and nitromethane being colorless liquids. As is further described hereinbelow in the next procedure (that is, procedure (b)), disappearance of the red to brown color of the initial mixture of water, nitromethane, and bromine, and of the subsequent reaction mixture of water, nitromethane, bromine, and bromopicrin (being an oily colorless liquid at room temperature), formed therefrom, is an accurate and precise (reproducible) indicator of completion of reaction of an alkaline substance with the bromine, and consequently with the nitromethane, in a reaction mixture, for forming high purity bromopicrin in high (essentially, theoretical stoichiometric) yield.

(b) Subsequent to Providing the Mixture, Adding an Aqueous Solution of an Alkaline Substance to the Mixture, to Thereby Provide a Reaction Mixture Containing the Bromopicrin, the Adding being Performed Such that No Excess of the Alkaline Substance Occurs in the Reaction Mixture During the Adding of the Aqueous Solution:

In procedure (b), there is adding an aqueous solution of an alkaline substance to the mixture of nitromethane and bromine subsequently formed and provided by the previous procedure (that is, procedure (a)), to thereby provide a reaction mixture containing the bromopicrin. Accordingly, for the preferred embodiment of the process of the present invention wherein water is included in the mixture of nitromethane and bromine, then, in procedure (b), preferably, there is adding an aqueous solution of an alkaline substance to the mixture of water, nitromethane, and bromine formed and provided by the previous procedure (that is, procedure (a)), to thereby provide a reaction mixture containing the bromopicrin.

Preferably, the alkaline substance is essentially any type of alkaline material which is capable of rapidly and selectively reacting with the bromine contained in the mixture of nitromethane and bromine (while in the presence of water and nitromethane), for forming one or more bromine-containing chemical intermediate(s), for example, a metal hypobromite formed by reaction between a metal alkali hydroxide, such as sodium hydroxide or potassium hydroxide and bromine, as generally indicated by chemical equation [2]:

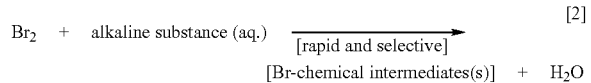

In turn, the one or more bromine-containing chemical intermediate(s), in the presence of water, selectively react(s) with the already present nitromethane, for selectively forming the desired high purity bromopicrin product in high (essentially, theoretical stoichiometric) yield, as generally indicated by chemical equation [3]:

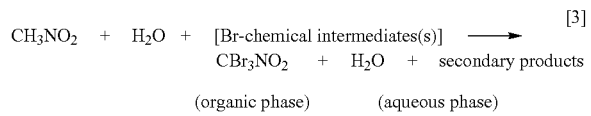

For example, the alkaline substance is selected from the group consisting of metal alkali hydroxides, alkaline earth hydroxides, and combinations thereof. Exemplary metal alkali hydroxides are lithium hydroxide [LiOH], sodium hydroxide [NaOH], and potassium hydroxide [KOH]. Exemplary alkaline earth hydroxides are magnesium hydroxide [$Mg(OH)_2$], calcium hydroxide [$Ca(OH)_2$], strontium hydroxide [$Sr(OH)_2$], and barium hydroxide [$Ba(OH)_2$].

For performing procedure (b) of the process of the present invention, preferably, the alkaline substance is a metal alkali hydroxide selected from the group consisting of lithium hydroxide [LiOH], sodium hydroxide [NaOH], potassium hydroxide [KOH], and a combination thereof. More preferably, the alkaline substance is a metal alkali hydroxide selected from the group consisting of sodium hydroxide [NaOH], potassium hydroxide [KOH], and a combination thereof. Most preferably, the alkaline substance is sodium hydroxide [NaOH].

Sodium hydroxide is preferred over potassium hydroxide for performing this procedure, mainly based on chemical process economics. For comparable quality (purity), and concentration, sodium hydroxide costs less than potassium hydroxide.

As further described and exemplified hereinbelow, the concentration of the alkaline substance in the aqueous solution of the alkaline substance, which is added to the mixture of nitromethane and bromine (absent of water, or including water), is a secondary process parameter for determining selectivity of the reaction for producing bromopicrin.

The alkaline substance in the aqueous solution of the alkaline substance (which is added to the mixture of nitromethane and bromine) has a concentration which can be expressed in units of, for example, percent (weight/weight) or (w/w), corresponding to expressing as a percent the ratio of the weight of the alkaline substance and the weight of the aqueous solution of the alkaline substance (that is, the combined weight of the alkaline substance in the aqueous solution and the weight of the water in the aqueous solution).

In general, the concentration of the alkaline substance in the aqueous solution of the alkaline substance can be varied. The concentration of the alkaline substance in the aqueous solution of the alkaline substance is in a range of, preferably, between about 5 percent (weight/weight) and about 50 percent (weight/weight), more preferably, between about 25 percent (weight/weight) and about 40 percent (weight/weight). The optimum concentration of the alkaline substance in the aqueous solution of the alkaline substance is about 35 percent (weight/weight).

For an exemplary embodiment of the process of the present invention, wherein the alkaline substance is a metal alkali hydroxide, such as sodium hydroxide or potassium hydroxide, the concentration of the metal alkali hydroxide (sodium hydroxide or potassium hydroxide) in the aqueous solution of the metal alkali hydroxide is in a range of, preferably, between about 5 percent (weight/weight) and about 50 percent (weight/weight), more preferably, between about 25 percent (weight/weight) and about 40 percent (weight/weight). The optimum concentration of the metal alkali hydroxide (sodium hydroxide or potassium hydroxide) in the aqueous solution of the metal alkali hydroxide is about 35 percent (weight/weight).

As previously described hereinabove, in general, the (initial) temperature of the mixture of nitromethane and bromine, (absent of water, or including water), as formed and provided according to procedure (a), can be varied, and is in a range of, preferably, between about 10° C. and about 50° C., and more preferably, between about 20° C. and about 25° C. (room temperature). Preferably, prior to performing procedure (b), the temperature of the mixture of nitromethane and bromine, (absent of water, or including water), is in a range of, preferably, between about 10° C. and about 50° C. Accordingly, for performing procedure (b) according to a batch mode type of operation, prior to performing procedure (b), preferably, the temperature of the mixture of nitromethane and bromine, (absent of water, or including water), in the reactor, is in a range of between about 10° C. and about 50° C.

In procedure (b), the temperature of the reaction (reaction temperature ($T_R$)) while bromopicrin is formed corresponds to the temperature of the reaction mixture containing bromopicrin so formed, maintained throughout adding of the aqueous solution of the alkaline substance to the mixture of nitromethane and bromine, or, preferably, throughout adding of the aqueous solution of the alkaline substance to the mixture of water, nitromethane, and bromine. The temperature of the reaction (reaction temperature ($T_R$)) is a primary process parameter for determining selectivity of the reaction for producing bromopicrin. Clearly, the temperature of the reaction (reaction temperature ($T_R$)) determines the kinetics, and therefore, the rate, of the reaction for producing bromopicrin, and is thus a primary process parameter for determining selectivity of the reaction for producing bromopicrin.

In general, the temperature of the reaction (reaction temperature ($T_R$)) maintained throughout adding of the aqueous solution of the alkaline substance to the mixture of nitromethane and bromine, or, preferably, throughout adding of the aqueous solution of the alkaline substance to the mixture of water, nitromethane, and bromine, and consequently, throughout forming the reaction mixture containing bromopicrin, can be varied. In procedure (b), the temperature of the reaction (reaction temperature ($T_R$)) is maintained in a range of, preferably, between about 20° C. and about 50° C., and more preferably, between about 35° C. and about 45° C.

For performing procedure (b), the actual temperature of the reaction (reaction temperature ($T_R$)), and range thereof, are maintained at values which depend upon several factors. Two main factors are the magnitude, and rate, respectively, of the eventual exothermic heat released during subsequent reaction between the added alkaline substance and the mixture of nitromethane and bromine, as the reaction mixture containing bromopicrin is formed, as generally indicated by chemical equations [2] and [3], above. An additional two main factors, which are complementary to the just stated two main factors, are the magnitude, and rate, respectively, of dissipation, transfer, or/and control, of the exothermic heat released during the reaction forming the bromopicrin. For example, for performing procedure (b) according to a batch mode type of operation, depending upon the just indicated main factors, the temperature of the reaction (reaction temperature ($T_R$)), and range thereof, are controlled and maintained at pre-determined values by setting the automatic chemical reactor temperature controller device at a pre-determined set point.

In procedure (b), the aqueous solution of the alkaline substance is controllably added to the mixture of nitromethane and bromine, or, preferably, controllably added to the mixture of water, nitromethane, and bromine, as formed and provided by procedure (a), in a manner such that no excess of the alkaline substance occurs in the reaction mixture containing the bromopicrin, during the adding of the aqueous solution of the alkaline substance.

A first reason for such control is that, procedure (b) is performed in a manner such that no excess of the alkaline substance occurs in the reaction mixture containing the bromopicrin, during the adding of the aqueous solution of the alkaline substance. As further described in detail hereinbelow, depending upon the actual alkaline substance used for performing procedure (b), the presence of excess alkaline substance in the reaction mixture containing bromopicrin can lead to undesirable reaction between the excess alkaline substance and the bromopicrin for forming impurities, thereby decreasing the purity and yield of the bromopicrin. A second reason for such control is that, depending upon actual operating conditions and process parameters, the reaction between the alkaline substance and the mixture of nitromethane and bromine for forming a reaction mixture containing bromopicrin can be relatively rapid, and accompanied by a corresponding rapid release of exothermic heat, and thus needs to be controlled.

The appropriate parameter used for controllably adding the aqueous solution of the alkaline substance to the mixture of nitromethane and bromine, or, preferably, controllably added to the mixture of water, nitromethane, and bromine, is the duration of the reaction (herein, also referred to as reaction time). The duration of the reaction (reaction time) is a secondary process parameter for determining selectivity of the reaction for producing bromopicrin. Clearly, the duration of the reaction (reaction time) is associated with the kinetics, and therefore, the rate, of the reaction for producing bromopicrin.

In procedure (b), the duration of the reaction (reaction time) corresponds to the time period taken or used, and thus, spanning, from the beginning of adding the aqueous solution of the alkaline substance to the mixture of nitromethane and bromine, or, preferably, to the mixture of water, nitromethane, and bromine, until the end of adding the aqueous solution of the alkaline substance to the reaction mixture of water, nitromethane, bromine, alkaline substance, and formed bromopicrin. At the end or completion of the duration of the reaction (reaction time), corresponding to the end or completion of adding the aqueous solution of the alkaline substance to the reaction mixture of water, nitromethane, bromine, alkaline substance, and formed bromopicrin, the bromine has completely reacted with (been consumed by) the alkaline substance, and consequently has completely reacted with (been consumed by) the nitromethane, for forming the bromopicrin product. The duration of the reaction (reaction time) is expressed in units of time, for example, minutes or hours.

In general, the duration of the reaction (reaction time) for forming the bromopicrin can be varied. In procedure (b), the duration of the reaction (reaction time) is in a range of, preferably, between about 0.5 hour and about 24 hours, more preferably, between about 1 hour and about 10 hours, and most preferably, between about 2 hours and about 6 hours.

For performing procedure (b) according to a batch mode type of operation, throughout the time period or duration of adding the aqueous solution of the alkaline substance to the mixture of nitromethane and bromine, preferably, the mixture of nitromethane and bromine, and consequently, the reaction mixture of water, nitromethane, bromine, alkaline substance, and formed bromopicrin, in the chemical reactor, are continuously mixed, for example, by stirring, in the chemical reactor, for example, by using an automatically controllable mechanical or electro-mechanical stirrer.

Mixing of the reaction mixture, in the chemical reactor, throughout the time period or duration of adding the aqueous solution of the alkaline substance to the mixture of nitromethane and bromine, maximizes contact, and therefore, reaction, between the alkaline substance and the mixture of nitromethane and bromine. Such mixing of the reaction mixture in the chemical reactor also helps to assure that no localized regions or points of the alkaline substance are formed in the chemical reactor, thereby, conforming with the important condition or limitation in procedure (b) that no excess of the alkaline substance occurs in the reaction mixture containing the bromopicrin, during the adding of the aqueous solution of the alkaline substance. Such mixing of the reaction mixture in the chemical reactor also helps to assure uniform heat distribution, throughout the volume of the chemical reactor, thereby providing a chemical environment in the chemical reactor for producing high purity bromopicrin in high (essentially, theoretical stoichiometric) yield.

As previously described hereinabove, in procedure (a), the mixture of water, nitromethane, and bromine, takes on a red to brown color, due to the red to brown color of liquid bromine along with the water and nitromethane being colorless liquids. In procedure (b), as the alkaline substance is added to the mixture, and consequently reacts therewith, for forming the reaction mixture containing bromopicrin, the red to brown color gradually fades and eventually disappears from the reaction mixture. Complete disappearance of the red to brown color of the reaction mixture of water, nitromethane, bromine, alkaline substance, and formed bromopicrin (being an oily colorless liquid at room temperature), is an accurate and precise (reproducible) indicator of completion of reaction of the alkaline substance with the bromine, and consequently with the nitromethane, in the reaction mixture, for forming high purity bromopicrin in high (essentially, theoretical stoichiometric) yield.

In procedure (b), the color of the reaction mixture containing bromopicrin can be monitored and measured, preferably, continuously, for accurately determining completion of reaction of the added alkaline substance with the bromine, and consequently with the nitromethane, in the reaction mixture. In general, monitoring and measuring the color of the reaction mixture containing bromopicrin can be performed by using human visual or/and machine (device) visual color monitoring and measuring means. For example, a chemical reactor which may be used for implementing the process of the present invention can be operatively constructed or fitted with, or/and operatively connected to, equipment, for example, machine visual color monitoring and measuring means, for enabling semi-automatic or fully automatic monitoring and measuring of the color of the contents inside the chemical reactor, throughout adding of the aqueous solution of the alkaline substance to the mixture of nitromethane and bromine. In this manner, complete disappearance of the red to brown color of the reaction mixture of water, nitromethane, bromine, alkaline substance, and formed bromopicrin (being an oily colorless liquid at room temperature), typically, quickly followed by formation of a yellowish color, can be accurately and precisely (reproducibly) determined, along with accurately and precisely indicating completion of reaction of the alkaline substance with the bromine, and consequently with the nitromethane, in the reaction mixture, for forming high purity bromopicrin in high (essentially, theoretical stoichiometric) yield.

As previously stated hereinabove, procedure (b) is performed in a manner such that no excess of the alkaline substance occurs in the reaction mixture containing the bromopicrin, during the adding of the aqueous solution of the alkaline substance. Accordingly, absence of excess alkaline substance in the reaction mixture containing bromopicrin prevents any possible undesirable reaction between excess alkaline substance and the bromopicrin, thereby preventing formation of impurities, thereby maximizing the purity and yield of the bromopicrin.

In procedure (b), complete disappearance of the red to brown color of the reaction mixture of water, nitromethane, bromine, alkaline substance, and formed bromopicrin, accurately and precisely indicates completion of reaction of the alkaline substance with the bromine, and consequently with the nitromethane, in the reaction mixture, for forming high purity bromopicrin in high (essentially, theoretical stoichiometric) yield. This also corresponds to completion of the duration of the reaction (reaction time), at which time there is terminating the adding of the aqueous solution of the alkaline substance to the reaction mixture of water, nitromethane, bromine, alkaline substance, and formed bromopicrin.

Based on the above described manner of performing procedure (a), and performing procedure (b), and based on the chemical reaction phenomena taking place during procedure (b), at this stage of procedure (b) in the overall process of preparing bromopicrin, the reaction mixture containing bromopicrin no longer includes meaningful quantities of bromine or alkaline substance.

The bromine is no longer present in the reaction mixture since the bromine has completely reacted with (been consumed by) the alkaline substance, and consequently with the nitromethane, for forming bromopicrin. The alkaline substance is no longer present in the reaction mixture since the alkaline substance has completely reacted with the bromine, and consequently with the nitromethane; for forming bromopicrin. Addition of the aqueous solution of the alkaline substance to the reaction mixture was terminated, thus, precluding introduction of additional alkaline substance to the reaction mixture, thereby assuring absence of excess alkaline substance in the reaction mixture containing the bromopicrin. Both the bromine and the alkaline substance have completely reacted with each other, in the presence of water, for forming one or more bromine-containing chemical intermediate(s), as generally indicated by chemical equation [2], hereinabove. In turn, the one or more bromine-containing chemical intermediate(s), in the presence of water, react with the already present nitromethane, for forming high purity bromopicrin in high (essentially, theoretical stoichiometric) yield, as generally indicated by chemical equation [3], hereinabove.

Thus, at this stage of procedure (b), the reaction mixture containing bromopicrin is characterized by including as primary products: bromopicrin [$CBr_3NO_2$] and water, and as secondary products: inorganic salt(s), in particular, bromide salt(s); inorganic oxidant(s), in particular, hypobromite, bromite, and bromate, oxidants; and trace quantities of organic or/and inorganic materials. Clearly the actual type and distribution of secondary products depends upon the actual type of alkaline substance included in the aqueous solution of the alkaline substance which is added to the mixture of nitromethane and bromine, and depends upon the actual operating conditions and process parameters used for performing procedures (a) and (b).

Based on hereinabove previously stated preferred, and more preferred, temperatures of the reaction (reaction temperature ($T_R$)), then, immediately following completion of the duration of the reaction (reaction time), the temperature of the reaction mixture containing bromopicrin is preferably above about 20° C., and more preferably above about 35° C., respectively. Thus, at this stage of procedure (b), optionally, and preferably, immediately following completion of the duration of the reaction (reaction time), the temperature of the reaction mixture containing bromopicrin is allowed to decrease on its own, or is controllably decreased, to room temperature (between about 20° C. and about 25° C.).

As previously stated hereinabove, for performing procedure (b), throughout the time period or duration of adding the aqueous solution of the alkaline substance to the mixture of nitromethane and bromine, preferably, the mixture of nitromethane and bromine, and consequently, the reaction mixture of water, nitromethane, bromine, alkaline substance, and formed bromopicrin, are continuously mixed. Thus, immediately following completion of the duration of the reaction (reaction time), corresponding to immediately following termination of adding the aqueous solution of the alkaline substance to the reaction mixture, mixing of the reaction mixture containing bromopicrin, in the chemical reactor, can be terminated.

Optionally, and preferably, immediately following completion of the duration of the reaction (reaction time), corresponding to immediately following termination of adding the aqueous solution of the alkaline substance to the reaction mixture containing bromopicrin, the reaction mixture is further mixed, for a period of time, for example, in a range of between about 0.25 hour and about 0.5 hour. Preferably, this further mixing of the reaction mixture is performed while the temperature of the reaction mixture containing bromopicrin is allowed to decrease on its own, or is controllably decreased, to room temperature.

Further mixing of the reaction mixture containing bromopicrin immediately following completion of the duration of the reaction (reaction time), corresponding to immediately following termination of adding the aqueous solution of the alkaline substance to the reaction mixture, further maximizes the probability that remnant or minute quantities of bromine or/and alkaline substance or/and nitromethane will react with each other, in particular, throughout the volume of the chemical reactor, thereby providing a chemical environment in the chemical reactor for producing high purity bromopicrin in high (essentially, theoretical stoichiometric) yield.

At the end of the above indicated period of time of mixing the reaction mixture containing bromopicrin, at this stage of performing procedure (b), the mixing is terminated. The reaction mixture containing bromopicrin, that is, containing a mixture of primary products: bromopicrin [$CBr_3NO_2$] and water, and secondary products: inorganic salt(s), inorganic oxidant(s), and trace quantities of organic or/and inorganic materials, is allowed to undergo phase separation and phase equilibrium.

During phase separation and equilibrium, the primary product bromopicrin, having a water solubility of about 1.5 grams per liter water at 20° C., and a specific gravity of 2.79, migrates into and becomes the heavier (lower) organic phase, while the primary product water and the secondary products migrate into and become the lighter (upper) aqueous phase, of the reaction mixture. Accordingly, the two phases, that is, the heavier (lower) organic phase (containing bromopicrin) and the lighter (upper) aqueous phase (containing water and secondary products), of the reaction mixture, are allowed to completely separate from each other, and are allowed to reach phase equilibrium.

In accordance with the process of preparing bromopicrin of the present invention, by performing hereinabove described procedures (a) and (b), ordinarily, the two phases, that is, the heavier (lower) organic phase (containing primary product bromopicrin) and the lighter (upper) aqueous phase (containing primary product water, and secondary products), of the reaction mixture, take on distinguishably different colors, that is, distinguishable by a human operator or/and machine (device).

The heavier (lower) organic phase (containing essentially pure bromopicrin) is ordinarily colorless (or lightly colored, depending upon the type and quantity of impurities present with the bromopicrin), due to pure bromopicrin being an oily colorless liquid at room temperature. The lighter (upper) aqueous phase (containing water and the secondary products) is ordinarily colored, due to the secondary products present in the water. For example, for an exemplary embodiment of the process of the present invention, wherein the alkaline substance is a metal alkali hydroxide, such as sodium hydroxide, the heavier (lower) organic phase (containing essentially pure bromopicrin, with relatively low quantities of impurities) takes on a yellowish color, whereas the lighter (upper) aqueous phase (containing water and the secondary products) takes on a orange or orange-like color. Clearly, this phenomenon can be used as a reliable (accurate and precise) indicator that the reaction mixture has attained complete phase separation and equilibrium.

In general, monitoring and measuring the distinguishably different colors of the two phases of the reaction mixture containing bromopicrin can be performed by using human visual or/and machine (device) visual color monitoring and measuring means. For example, a chemical reactor which may be used for implementing the process of the present invention can be operatively constructed or fitted with, or/and operatively connected to, equipment, for example, machine visual color monitoring and measuring means, for enabling semi-automatic or fully automatic monitoring and measuring of the colors of the contents inside the chemical reactor, as the reaction mixture attains complete phase separation and equilibrium. In this manner, attainment of complete phase separation and equilibrium of the two phases of the reaction mixture containing bromopicrin can be accurately and precisely (reproducibly) determined, thereby maximizing the yield of the high purity bromopicrin contained in the reaction mixture.

For attaining complete phase separation and equilibrium, the reaction mixture containing bromopicrin is allowed to stand (without mixing) for a period of time of at least about 1 minute, more preferably, at least about 10 minutes, at room temperature (between about 20° C. and about 25° C.).

From the time of attaining complete phase separation and equilibrium, the reaction mixture containing bromopicrin is no longer a mixture of two liquid phases, but, rather is composed of two 'separated' liquid phases, that is, the heavier (lower) organic phase (containing bromopicrin) and the lighter (upper) aqueous phase (containing water and secondary products):

Organic Phase: primary product bromopicrin (having purity equal to or greater than 96 weight percent, and as high as 99 weight percent, in terms of (weight bromopicrin/total weight of the organic phase).

Aqueous Phase: primary product water, and secondary products: inorganic salt(s), in particular, bromide salt(s); inorganic oxidant(s), in particular, hypobromite, bromite, and bromate, oxidants; and trace quantities of organic or/and inorganic materials.

(c) Collecting the Bromopicrin from the Reaction Mixture:

In procedure (c), there is collecting the bromopicrin from the reaction mixture containing bromopicrin provided by procedure (b). As previously stated hereinabove, the reaction mixture containing bromopicrin is no longer a mixture of two liquid phases, but, rather is composed of two 'separated' liquid phases, that is, the heavier (lower) organic phase (containing bromopicrin) and the lighter (upper) aqueous phase (containing water and secondary products).

In general, essentially any number and types of chemical collection procedures, methods, or techniques, including, for example, distillation or extraction, along with appropriately corresponding chemical collection equipment and associated hardware, which are known in the art of collecting a (liquid phase) organic chemical from the organic (liquid) phase of a liquid mixture containing two separate (liquid) phases (that is, the organic liquid phase and an aqueous liquid phase), can be used for performing procedure (c).

In accordance with the process of preparing bromopicrin of the present invention, by performing hereinabove described procedures (a) and (b), the bromopicrin so produced is the only organic compound in meaningful quantity contained in the heavier (lower) organic phase of the reaction mixture. Since the bromopicrin in the reaction mixture has a purity equal to or greater than 96 weight percent, and as high as 99 weight percent (weight bromopicrin/total weight of the organic phase), then, the heavier (lower) organic phase of the reaction mixture consists essentially only of bromopicrin. Therefore, performing procedure (c) of collecting the bromopicrin from the reaction mixture essentially corresponds to collecting the heavier (lower) organic phase (containing the bromopicrin) from the reaction mixture provided by procedure (b).

Accordingly, in general, essentially any number and types of chemical collection procedures, process, or techniques, including, for example, distillation or extraction, along with appropriately corresponding chemical collection equipment and associated hardware, which are known in the art of collecting an organic (liquid) phase from a liquid mixture containing two separate (liquid) phases (that is, the organic liquid phase and an aqueous liquid phase), can be used for performing procedure (c).

For performing procedure (c), the heavier (lower) organic phase (containing the bromopicrin) of the reaction mixture is directly collected from the reaction mixture. Preferably, the heavier (lower) organic phase containing the bromopicrin is directly collected via gravity, for example, by free or forced draining or pumping, from the reaction mixture. Since in the reaction mixture the organic phase containing the bromopicrin is the heavier (lower) phase and the aqueous phase containing water and secondary products is the lighter (upper) phase, the organic phase can be readily collected by exploiting the natural force of gravity.

For example, by implementing the process of preparing bromopicrin of the present invention according to a batch mode type of operation, ordinarily the chemical reactor is vertically positioned, whereby, in the chemical reactor, the heavier (lower) phase of the reaction mixture is the organic phase containing the bromopicrin, and the lighter (upper) phase of the reaction mixture is the aqueous phase containing water and secondary products. Accordingly, in such an embodiment, the heavier (lower) organic phase containing the bromopicrin can be selectively, freely or forcibly drained or pumped from the bottom end portion or outlet of the chemical reactor, while leaving the lighter (upper) aqueous phase (containing water and secondary products) in the chemical reactor for possible future analysis, treatment, or/and disposal.

For example, such draining or pumping can be accomplished by appropriately controlling the opening of a valve which is operatively positioned at, or connected to, the bottom end portion or outlet of the chemical reactor, and collecting or receiving the organic phase in an operatively positioned or connected collection or receiving vessel or container made of material (for example, glass), which is, preferably, essentially chemically inert to the organic phase containing the bromopicrin.

Simultaneously, there is monitoring and measuring at least one property, for example, color, conductivity, or/and density, of the collected liquid, which is accurately and reproducibly characteristic of the collected liquid, that is, the heavier (lower) organic phase containing the bromopicrin, until there appears sign or indication of no more organic phase remaining in the bottom portion of the chemical reactor. Preferably, this corresponds to immediately before there appears first sign or indication of the aqueous phase entering the bottom end portion or outlet of the chemical reactor, at which time the draining or pumping of the heavier (lower) organic phase containing the bromopicrin from the chemical reactor is terminated by appropriately controlling the closing of the valve.

The collected organic phase containing the bromopicrin is used 'as is', stored 'as is' in the collection or receiving vessel or container, or transferred to a more suitable storage vessel or container, and then stored in an appropriate chemical storage environment. Suitable storage conditions for bromopicrin are in a low light transmitting container (for example, an opaque brown glass bottle), preferably unexposed to sunlight, at room temperature (that is, between about 20° C. and about 25° C.), and away from potentially flammable or explosive conditions. Under such storage conditions, bromopicrin is relatively stable and remains highly pure for up to at least several months.

Procedure (c) in the process of preparing bromopicrin of the present invention is an industrially applicable, reproducible, safe, environmentally friendly, and cost effective, procedure for collecting the high purity bromopicrin produced therefrom. The organic phase containing the bromopicrin is directly collected from the reaction mixture, without subjecting the organic phase to distillation or extraction, for obtaining near quantitative (theoretical stoichiometric) yield of bromopicrin having a purity equal to or greater than 96 weight percent, and as high as 99 weight percent. This aspect of the present invention results in precluding the need for including a distillation or extraction procedure along with relatively expensive distillation or extraction equipment, as well as costs involved for operating and maintaining thereof. This aspect also results in precluding the need for handling and taking into account the affects, in particular, as relating to health and safety, of the potentially hazardous (highly energetic) bromopicrin product during distillation or extraction conditions, as well as of the potentially hazardous and waste generating extraction solvent.

Optional Additional Procedures of the Process of Preparing Bromopicrin:

In general, the process of preparing bromopicrin of the present invention may include any number and types of optional additional procedures, depending at least partly on the actual operating conditions and process parameters used for implementing the process, and the results obtained therefrom, and depending upon the actual needs, requirements, and objectives, of a particular application involving implementation of the present invention.

Two exemplary categories of such optional additional procedures of preparing bromopicrin, in accordance with the present invention, are based on various different types or ways of processing the bromopicrin, and processing the aqueous phase, obtained from procedure (c). The first exemplary category of such optional additional procedures is based on performing quantitative composition analysis of the bromopicrin, and on the aqueous phase, obtained from procedure (c), in particular, with regard to quantitatively determining the composition of the bromopicrin, and of the aqueous phase. The second exemplary category of such optional additional procedures is based on treating the aqueous phase obtained from procedure (c), in particular, with regard to treating the bromine-containing inorganic oxidants and the organic materials contained in the aqueous phase. Each of these exemplary categories of such optional additional procedures of the process of preparing bromopicrin of the present invention is described immediately below.

Quantitative Composition Analysis of the Bromopicrin Obtained from Procedure (c):

Optionally, and preferably, there is performing quantitative composition analysis on the bromopicrin (corresponding to the heavier (lower) phase of the reaction mixture) collected during procedure (c), for the main objective of determining the actual purity of the collected bromopicrin. In general, essentially any number and types of chemical or/and physical analytical procedures, process, or techniques, including, for example, chromatography (in particular, gas chromatography (GC)) or/and spectroscopy, along with appropriately corresponding chemical or/and physical analytical equipment, instruments, reagents, and, associated hardware and software, which are known in the art of quantitative composition analysis of a highly pure liquid phase organic compound, which may contain relatively small quantities (for example, less than about 5 weight percent) of various organic or/and inorganic chemicals, can be used for performing this procedure.

Performing this procedure results in determining that the bromopicrin prepared in accordance with the process of the present invention, typically has a purity equal to or greater than 96 weight percent, and as high as 99 weight percent, in terms of weight bromopicrin/total weight of the organic phase. Typically, the main small quantity impurities in the bromopicrin are organic compounds, in particular, the reactant nitromethane [$CH_3NO_2$], and the reaction by-products dibromonitromethane [$CHBr_2NO_2$] and tetrabromodinitroethane [$C_2Br_4(NO_2)_2$] or [$NO_2Br_2C-CBr_2NO_2$].

The reaction by-product tetrabromodinitroethane is most likely formed during procedure (b) of adding the aqueous solution of the alkaline substance to the mixture of nitromethane and bromine, as a result of reaction between bromopicrin and the alkaline substance. Thus, justifying the need of including in procedure (b) the condition that procedure (b) be performed in a manner such that no excess of the alkaline substance occurs in the reaction mixture containing the bromopicrin, during the adding of the aqueous solution of the alkaline substance. Absence of excess alkaline substance in the reaction mixture containing bromopicrin prevents any possible undesirable reaction between excess alkaline substance and the bromopicrin, thereby preventing formation of impurities, such as the reaction by-products dibromonitromethane and tetrabromodinitroethane, thereby maximizing the purity and yield of the bromopicrin.

Quantitative Composition Analysis of the Aqueous Phase Obtained from Procedure (c):

As stated hereinabove, while performing procedure (c), the heavier (lower) organic phase containing the bromopicrin is selectively, freely or forcibly drained or pumped from the bottom end portion or outlet of the chemical reactor, while leaving the lighter (upper) aqueous phase (containing water and secondary products) in the Chemical reactor for possible future analysis, treatment, or/and disposal.

Thus, optionally, and preferably, there is collecting the lighter (upper) aqueous phase (containing water and secondary products) which was left in the chemical reactor, and performing quantitative composition analysis on the collected aqueous phase, for the main objective of determining the chemical composition and make-up of the aqueous phase. In general, essentially any number and types of chemical or/and physical analytical procedures, process, or techniques, along with appropriately corresponding chemical or/and physical analytical equipment, instruments, reagents, and, associated hardware and software, which are known in the art of quantitative composition analysis of an aqueous phase material which contains various inorganic and organic chemicals, can be used for performing this procedure.

Performing this procedure results in determining that the secondary products contained in the aqueous phase obtained in accordance with the process of the present invention, are typically inorganic salt(s), in particular, bromide salt(s); inorganic oxidant(s), in particular, hypobromite, bromite, and bromate, oxidants; and trace quantities of organic or/and inorganic materials. For example, for an exemplary embodiment of the process of the present invention, wherein the alkaline substance is a metal alkali hydroxide, such as sodium hydroxide, as indicated by chemical equation [4], above, typically, the main secondary products contained in the aqueous phase are the inorganic salt sodium bromide [NaBr]; the bromine-containing inorganic oxidants [NaBrO], [$NaBrO_2$], and [$NaBrO_3$]; and organic materials in a relatively trace quantity, that is, up to about 1000 ppm, based on bromopicrin [$CBr_3NO_2$].

Treating the Aqueous Phase Obtained from Procedure (c):

As stated hereinabove, while performing procedure (c), the heavier (lower) organic phase containing the bromopicrin is selectively, freely or forcibly drained or pumped from the bottom end portion or outlet of the chemical reactor, while leaving the lighter (upper) aqueous phase (containing water and secondary products: inorganic salt(s), inorganic oxidant(s), and trace quantities of organic or/and inorganic materials) in the chemical reactor for possible future analysis, treatment, or/and disposal.

Unless there be identified a suitable use of such an aqueous phase obtained from procedure (c), or a suitable use of a treated form of such an aqueous phase, for example, via recycling, for use in some other industrial application, then, ordinarily, the aqueous phase is considered waste, and is disposed of using an appropriate waste disposal procedure, process, or technique, along with appropriately corresponding waste disposal reagents, equipment, and instruments, which are known in the art of disposing of aqueous phase materials which contain various inorganic and organic chemicals. However, before disposing of the aqueous phase, there is a need for taking into account the handling involved and the affects, in particular, as relating to health and safety, by disposing of such an aqueous phase. For example, national or/and local environmental rules and regulations may restrict or prohibit disposing of any one or more of the inorganic or/and organic components or materials of the aqueous phase obtained from procedure (c), at concentration levels which are typically present in the aqueous phase. Accordingly, there may by a need for treating the aqueous phase obtained from procedure (c).

Thus, optionally, and preferably, there is collecting the lighter (upper) aqueous phase (containing water and secondary products) which was left in the chemical reactor, and treating the collected aqueous phase, for the main objective of providing a treated form of the aqueous phase which is more amenable and environmentally suitable (friendly) to waste disposal than the untreated form of the collected aqueous phase, or, which is suitable or potentially suitable, for example, via recycling, for use in some other industrial procedure or application, for example, isolation of sodium bromide [NaBr], production of bromine [$Br_2$], or/and production of hydrobromic acid (hydrogen bromide) [HBr].

In general, essentially any number and types of chemical or/and physical treating procedures, process, or techniques, along with appropriately corresponding chemical or/and physical treating reagents, equipment, and instruments, which are known in the art of chemical or/and physical treating of an aqueous phase material which contains various inorganic and organic chemicals, can be used for performing this procedure. Preferably, there is chemically treating the aqueous phase obtained from procedure (c), for example, by adding at least one chemical treating agent to the aqueous phase obtained from procedure (c). A main objective of chemically treating the aqueous phase is to chemically treat (for example, via neutralization or/and reduction reactions) the bromine-containing inorganic oxidants (for example, [NaBrO], [NaBrO$_2$], and [NaBrO$_3$]), and the organic materials ([CBr$_3$NO$_2$], [CNaBr$_2$NO$_2$], [CHNaBrNO$_2$], and [CH$_2$NaNO$_2$], along with a relatively trace quantity, on the order of about 1000 ppm, of bromopicrin [CBr$_3$NO$_2$]).

Accordingly, for performing this procedure, in general, the chemical treating agent(s) is (are) essentially any type(s) or form(s) (liquid, solid, or/and gas phase(es)) of material(s) which is (are) capable of chemically treating an aqueous phase material which includes halogen- (in particular, bromine-) containing inorganic oxidants, and various organic materials, in a manner such that there is eliminating or at least minimizing the oxidizing power of such inorganic oxidants, and there is reducing the potential hazard or toxicity of the organic materials, in the aqueous phase (that is, in combination with the chemical treating agent), without imparting other potentially undesirable or/and hazardous characteristics, properties, or behavior, to the aqueous phase. An exemplary chemical treating agent, which is suitable for chemically treating the aqueous phase obtained from procedure (c), is an aqueous solution of sodium hydrogen sulphite (SBS— sodium bisulfate) [NaHSO$_3$], for example, with an SBS concentration of about 20 weight percent (weight SBS/total weight aqueous solution).

Chemically treating the aqueous phase in the above described manner typically results in the production of an aqueous mixture of a variety of one or more bromine-containing inorganic salts, for example, sodium bromide [NaBr]; sodium hydrogen sulfate [NaHSO$_4$], and sodium sulfate [Na$_2$SO$_4$]; organic material, for example, nitromethane [CH$_3$NO$_2$]; and a bromine-containing acid, in particular, hydrobromic acid (hydrogen bromide) [HBr]. As a result of the production of [NaHSO$_4$] and hydrobromic acid [HBr], the pH of the chemically treated aqueous phase may decrease down to of the order of less than about 1. Thus, in such a case, optionally, and preferably, there is neutralizing the acidity of the chemically treated aqueous phase, by adding an acid neutralizing agent to the chemically treated aqueous phase. Accordingly, for example, there is adding an aqueous solution of an alkaline substance, such as an aqueous solution of a metal alkali hydroxide, for example, sodium hydroxide [NaOH] or potassium hydroxide [KOH], to the chemically treated aqueous phase.

Accordingly, for example, for an exemplary embodiment of the process of the present invention, wherein the alkaline substance (for chemical treating) is a metal alkali hydroxide, such as sodium hydroxide, there is adding an aqueous solution of sodium hydroxide (for example, having a concentration of about 35 percent (weight/weight) or (w/w), corresponding to expressing as a percent the ratio of the weight of the alkaline substance and the weight of the water in the aqueous solution of the alkaline substance) to the chemically treated aqueous phase. The [NaHSO$_4$] and hydrobromic acid [HBr] present in the chemically treated aqueous phase react with the metal alkali hydroxide, for example, sodium hydroxide [NaOH], to form [NaBr], [Na$_2$SO$_4$], and [Na$_2$SO$_3$], in the resulting neutralized chemically treated aqueous phase, along with increasing the pH thereof to a value in a range of, preferably, between about 6 and 8.

Optionally, and preferably, there is performing chemical or/and physical analyses on the above obtained chemically treated or/and neutralized forms of the aqueous phase, for the main objective of quantitatively determining the chemical composition and make-up thereof.

Thus, the lighter (upper) aqueous phase (containing water and secondary products) of the reaction mixture which is obtained by implementing the process of preparing bromopicrin in accordance with the present invention, is chemically treated, and, optionally, and preferably, then neutralized, for being converted to a form which is more amenable and environmentally suitable (friendly) to waste disposal than the untreated form of the collected aqueous phase, or, which is suitable or potentially suitable, for example, via recycling, for use in some other industrial application.

According to another main aspect of the present invention, there is provision of bromopicrin having a purity equal to or greater than 96 weight percent. Moreover, bromopicrin having a purity equal to or greater than 99 weight percent can be obtained by implementing the process of the present invention.

In accordance with the process of preparing bromopicrin of the present invention, by performing hereinabove described procedures (a), (b), and (c), where, in procedures (a) and (b) the bromopicrin is formed in a reaction mixture, and in procedure (c) the bromopicrin is collected from the heavier (lower) organic phase (containing bromopicrin) of the reaction mixture provided by procedure (b), there is obtaining near quantitative (theoretical stoichiometric) yield of bromopicrin having a purity equal to or greater than 96 weight percent, and as high as 99 weight percent, in terms of weight bromopicrin/total weight of the organic phase.

Performing chemical or/and physical analyses on the bromopicrin collected during procedure (c), as described hereinabove, and exemplified hereinbelow, results in determining that the bromopicrin prepared in accordance with the process of the present invention, typically has a purity equal to or greater than 96 weight percent, and as high as 99 weight percent. Typically, the main small quantity impurities in the bromopicrin are organic compounds, in particular, the reactant nitromethane [CH$_3$NO$_2$], and the reaction by-products dibromonitromethane [CHBr$_2$NO$_2$] and tetrabromodinitroethane [C$_2$Br$_4$(NO$_2$)$_2$] or [NO$_2$Br$_2$C—CBr$_2$NO$_2$].

The bromopicrin obtained by implementing the process of the present invention is used 'as is', or stored 'as is' in a vessel or container, in an appropriate chemical storage environment. Suitable storage conditions for bromopicrin are in a low light transmitting container (for example, an opaque brown glass bottle), preferably unexposed to sunlight, at room temperature (between about 20° C. and about 25° C.), and away from potentially flammable or explosive conditions. Under such storage conditions, bromopicrin is relatively stable and remains highly pure for up to at least several months.

Above illustratively described novel and inventive aspects and characteristics, and advantages thereof, of the present invention further become apparent to one ordinarily skilled in the art upon examination of the following examples, which are not intended to be limiting. Additionally, each of the various embodiments and aspects of the present invention as delineated herein above and as claimed in the claims section below finds experimental support in the following examples. Reference is now made to the following examples, which together with the above description, illustrate the invention in a non-limiting fashion.

EXAMPLES

Preparing Bromopicrin Using a Metal Alkali Hydroxide as the Alkaline Substance, and the Bromopicrin Prepared Therefrom Highly pure bromopicrin was prepared, in accordance with the present invention, using a metal alkali hydroxide, in particular, sodium hydroxide, as the alkaline substance in the aqueous solution of the alkaline substance which is added to the mixture of nitromethane and bromine, as indicated by chemical equation [4], hereinabove, wherein water is included in the mixture. Several separate experimental 'runs' of implementing the present invention were performed using a laboratory scale 1 liter size chemical reactor, and a mini-pilot plant scale 16 liter size chemical reactor.

Materials and Experimental Process

Chemical Reagents:

Nitromethane [$CH_3NO_2$], in the liquid phase, was obtained from Fluka (assay of at least 97 weight percent), and from Aldrich (assay of at least 96 weight percent). Sodium hydroxide [NaOH], in the form of pellets, with an assay of at least 97 percent, was obtained from Frutarom, Israel. Potassium hydroxide [KOH], in the form of flakes, AR (analytical reagent) grade, was obtained from Frutarom, Israel. Bromine [$Br_2$], in the liquid phase, with an assay of at least 99 weight percent, was obtained from Dead Sea Bromine Group (DSBG), Israel. Sodium hydrogen sulphite (SBS—sodium bisulfate) [$NaHSO_3$], with a minimum $SO_2$ content of 58.5 percent, was obtained from Aldrich.

The following additional chemicals were used for performing the analytical (gas chromatographic) procedures:

Bromopicrin [$CBr_3NO_2$], monobromonitromethane [$CH_2BrNO_2$], dibromonitromethane [$CHBr_2NO_2$], and tetrabromodinitroethane [$C_2Br_4(NO_2)_2$], were obtained from the organic phase product collected during implementation of the process of the present invention. Samples of the collected organic phase (containing the bromopicrin) product of the reaction mixture were subjected to vacuum distillation and appropriate fractions of each pure compound were collected. Identity of each pure compound was verified by using gas chromatography-mass spectrometry (GC-MS) and nuclear magnetic resonance (NMR).

Dichloromethane (methylene chloride), analytical reagent grade, was obtained from Frutarom, Israel.

Chemical Reactors:

Two sizes of a vertically positioned chemical reactor were used: a laboratory scale 1 liter size chemical reactor, and a mini-pilot plant scale 16 liter size chemical reactor. Each vertically positioned chemical reactor was jacketed and operatively fitted with a mechanical stirrer, and a Lauda automatic chemical reactor temperature controller device operative with variable chemical reactor temperature set point (s.p.), which, in turn, was operatively connected to an appropriate power supply.

Analytical Procedures:

A gas chromatography chemical analysis procedure was performed on the heavier (lower) organic phase (containing bromopicrin) of the reaction mixture, collected during the process, for determining bromopicrin purity and compositions thereof. An HP 5890 gas chromatograph was used in the procedure.

Temperature Program (BPK process): Initial temperature of 50° C.; held for 2 min; then raised to 300° C. at 10° C./minute, and held for 5 minutes.

Injector: 200° C.

Detector: 325° C.

Split ratio: 1:100.

Injection amounts: 1 µl (20-25%, w/w solution in dichloromethane.

Column: RTx-1, capillary, 15 m×0.25 mm×0.25µ, 100% dimethylpolysiloxane packing. A calibration curve was plotted for nitromethane, from which the response factor was calculated.

Column retention times of the components were as follows. nitromethane: 0.9 minutes; monobromonitromethane: 2.0 minutes; dibromonitromethane: 3.8 minutes; bromopicrin: 6.8 minutes; and tetrabromodinitroethane: 8.9 minutes.

Standard wet chemistry types of analytical procedures were performed on the lighter (upper) aqueous phase (containing water and secondary products) of the reaction mixture, collected during the process, and on the treated aqueous phase, for determining chemical compositions and make-up thereof.

Preparation of Bromopicrin:

The general process used for performing each of several experimental runs, using the above described vertically positioned 1 liter laboratory scale, and 16 liter mini-pilot plant, batch type chemical reactors, is as follows. For the purpose of brevity, while maintaining clarity of understanding the Examples, those procedures or reaction conditions which were specific to the runs performed using the 1 liter laboratory scale chemical reactor are immediately followed by the parenthetical phrase (1 liter laboratory scale chemical reactor), and those procedures or reaction conditions which were specific to the runs performed using the 16 liter mini-pilot plant scale chemical reactor are immediately followed by the parenthetical phrase (16 liter mini-pilot plant chemical reactor).

At room temperature (between about 20° C. and about 25° C.) and with continuous stirring, a mixture of water, nitromethane, and bromine, with the molar ratio of bromine and nitromethane being about 3, was prepared by adding a quantity of water to the vertically positioned chemical reactor, followed by adding a quantity of nitromethane to the water, for forming a mixture of water and nitromethane in the chemical reactor, followed by adding a quantity of bromine to the mixture of water and nitromethane in the chemical reactor. No organic solvent was added to the mixture in the chemical reactor. The mixture of water, nitromethane, and bromine, took on a red to brown color.

While the mixture of water, nitromethane, and bromine, in the chemical reactor, was continuously stirred, prior to adding an aqueous solution of sodium hydroxide, the temperature of the mixture was typically increased (1 liter laboratory scale chemical reactor), or typically decreased (16 liter mini-pilot plant scale chemical reactor), by adjusting the Lauda automatic chemical reactor temperature controller device to be operative at a pre-determined chemical reactor temperature set point (s.p.).

While maintaining continuous stirring of the contents of the chemical reactor, subsequent to forming the mixture of water, nitromethane, and bromine, in the chemical reactor, the aqueous solution of sodium hydroxide, having a concentration of about 34-35 weight percent (weight sodium hydroxide/weight aqueous solution) was controllably added, at a mass flow rate of about 100 g/hour (1 liter laboratory scale chemical reactor), or at a mass flow rate of about 1.28 kg/hour (16 liter mini-pilot plant scale chemical reactor), to the mixture of water, nitromethane, and bromine, in the chemical reactor, to thereby provide a reaction mixture containing the bromopicrin. This procedure was performed in a manner such that no excess of the alkaline substance occurred in the reaction mixture containing the bromopicrin, during the adding of the aqueous solution of the alkaline substance. Mixing of the reaction mixture in the chemical reactor helped to assure that no localized regions or points of the alkaline substance were formed in the chemical reactor, during the adding of the aqueous solution of the sodium hydroxide, thereby preventing undesirable reaction between any excess sodium hydroxide and the newly formed bromopicrin which could have formed impurities. Such mixing also helped to assure uniform heat distribution throughout the volume of the chemical reactor, thereby providing a chemical environment in the chemical reactor for producing high purity bromopicrin in high (essentially, theoretical stoichiometric) yield.

While maintaining continuous stirring of the contents of the chemical reactor, the temperature of the reaction (reaction temperature ($T_R$)) throughout adding of the aqueous solution of the alkaline substance to the mixture of water, nitromethane, and bromine, and consequently, throughout forming the reaction mixture containing bromopicrin, was maintained in a range of between about 24° C. and about 48° C. (1 liter laboratory scale chemical reactor), or in a range of between about 22° C. and about 45° C. (16 liter mini-pilot plant scale chemical reactor).

As the sodium hydroxide was added to the mixture, and consequently reacted therewith, for forming the reaction mixture containing bromopicrin, the red to brown color gradually faded and eventually disappeared from the reaction mixture. The reaction was exothermic and very fast, and terminated immediately after stopping the addition of the aqueous solution of sodium hydroxide. Complete disappearance of the red to brown color of the reaction mixture of water, nitromethane, bromine, sodium hydroxide, and the formed bromopicrin, typically, quickly followed by formation of a yellowish color, was used as an accurate and precise (reproducible) indicator of completion of reaction of the sodium hydroxide with the bromine, and consequently with the nitromethane, in the reaction mixture, for forming the high purity bromopicrin in high (essentially, theoretical stoichiometric) yield.

The duration of the reaction (reaction time, or Time (as indicated in the Tables hereinbelow), corresponding to the time period spanning from the beginning of adding the aqueous solution of the sodium hydroxide to the mixture of water, nitromethane, and bromine, to the end of adding the aqueous solution of the sodium hydroxide to the reaction mixture of water, nitromethane, bromine, sodium hydroxide, and formed bromopicrin, at which time the bromine was completely reacted with (been consumed by) the sodium hydroxide, and consequently has completely reacted with (been consumed by) the nitromethane, for forming the bromopicrin product, was in a range of between about 3.5 hours and about 4 hours (1 liter laboratory scale chemical reactor), or in a range of between about 4 hours and about 6 hours (16 liter mini-pilot plant scale chemical reactor).

Immediately following completion of the duration of the reaction (reaction time), corresponding to immediately following termination of adding the aqueous solution of the sodium hydroxide to the reaction mixture, the reaction mixture containing bromopicrin, in the chemical reactor, was further mixed, for a period of time of about 30 minutes, while the temperature of the reaction mixture containing bromopicrin was decreased to room temperature (between about 20° C. and about 25° C.).

Mixing of the reaction mixture containing bromopicrin was terminated. The reaction mixture containing bromopicrin, that is, containing a mixture of primary products: bromopicrin [$CBr_3NO_2$] and water, and secondary products: inorganic salt(s), inorganic oxidant(s), and trace quantities of organic or/and inorganic materials, was allowed to undergo phase separation and equilibrium. The primary product bromopicrin, having a water solubility of about 1.5 grams per liter water at 20° C., and a specific gravity of 2.79, migrated into and became the heavier (lower) organic phase, while the primary product water and the secondary products migrated into and became the lighter (upper) aqueous phase, of the reaction mixture.

The heavier (lower) organic phase containing the bromopicrin was selectively collected, via draining or pumping, from the bottom end portion or outlet of the vertically positioned chemical reactor, while initially leaving behind the lighter (upper) aqueous phase (containing water and secondary products) in the chemical reactor. Simultaneously, there was monitoring and measuring at least one property, for example, color, conductivity, or/and density, of the collected liquid, which was accurately and reproducibly characteristic of the collected liquid, that is, the heavier (lower) organic phase containing the bromopicrin, until there appeared sign or indication of no more organic phase remaining in the bottom portion of the chemical reactor. This corresponded to immediately before there appeared first sign or indication of the aqueous phase entering the bottom end portion or outlet of the chemical reactor, at which time the draining or pumping of the heavier (lower) organic phase containing the bromopicrin from the chemical reactor was terminated.

Thereafter, the lighter (upper) aqueous phase (containing water and secondary products), which was initially left behind in the chemical reactor, was collected from the chemical reactor, for determining the chemical composition and make-up of the aqueous phase.

The collected heavier (lower) organic phase (containing bromopicrin) of the reaction mixture was subjected to the above described gas chromatography chemical analysis procedure, for determining bromopicrin purity and compositions thereof. The collected lighter (upper) aqueous phase (containing water and secondary products) of the reaction mixture was subjected to standard wet chemistry types of analytical procedures.

The collected aqueous phase was chemically treated using an aqueous solution of sodium hydrogen sulphite (SBS—sodium bisulfate [$NaHSO_3$], with SBS concentration of about 20 weight percent (weight SBS/total weight aqueous solution), which neutralized or/and reduced the bromine-containing inorganic oxidants. The treated aqueous phase was also subjected to standard wet chemistry types of analytical procedures.

Chemically treating the aqueous phase resulted in the production of an aqueous mixture of [$NaHSO_4$] and hydrobromic acid (hydrogen bromide) [HBr], along with a decrease in the pH of the chemically treated aqueous phase down to about 1. Thus, the acidity of the chemically treated aqueous phase was neutralized using the aqueous solution of sodium hydroxide [NaOH] (concentration of about 34-35 percent (weight sodium hydroxide/weight aqueous solution)).

Experimental Results

Laboratory Scale (1 Liter Size Chemical Reactor):

Weights of starting materials (reactants) and products, and reaction conditions, are listed in Table 1. Composition analysis of the collected heavier (lower) organic phase (containing bromopicrin) of the reaction mixture is listed in Table 2. In Table 2, purity of the bromopicrin (BP) is listed in terms of weight percent, corresponding to the ratio of the weight of bromopicrin in the (collected) organic phase and the total weight of the (collected) organic phase. Composition analysis of the collected lighter (upper) aqueous phase (containing water and secondary products) of the reaction mixture, before and after chemical treatment, is listed in Table 3. FIG. 1 is a flow block diagram of the actual scheme and procedures of an example of implementing the present invention using the laboratory scale 1 liter size chemical reactor, for reaction conditions and results of an exemplary run, Run no. 38585-3 (indicated in bold in Tables 1, 2, and 3). In FIG. 1, g=grams; %=percent; h=hours; RT=room temperature; s.p.=temperature set point; org=organic; aq.=aqueous; d=density; ml=milliliter; Assay=purity; and T=treated.

TABLE 1

Weights of starting materials and products, and reaction conditions.

| Run no. | $H_2O$ grams | NM grams | $Br_2$ grams | Aq. NaOH percent | Aq. NaOH grams | $T_R$ °C. | Time hours | BP grams | Aq. phase grams |
|---|---|---|---|---|---|---|---|---|---|
| 38479-33 | 100 | 61 | 499 | 34.2 | 398 | 24-29 | 3.5 | 273 | 781 |
| 38479-35 | 100 | 61 | 499 | 34.2 | 394 | 33-38 | 3.5 | 274 | 769 |
| 38585-2  | 100 | 61 | 500 | 34.2 | 390 | 33-37 | 4.0 | 277 | 763 |
| 38585-3  | 100 | 61 | 500 | 34.2 | 390 | 35-39 | 4.0 | 278 | 762 |
| 38585-5  | 100 | 61 | 500 | 35.3 | 373 | 35-39 | 4.0 | 279 | 743 |
| 38585-6  | 100 | 61 | 500 | 35.3 | 372 | 42-48 | 4.0 | 279 | 742 |

$T_R$ = temperature of the reaction (reaction temperature).
NM = nitromethane, BP = bromopicrin.

TABLE 2

Analysis of the organic phase (containing bromopicrin).

| Sample no. | Weight grams | Composition, percent by GC* NM | DBNM | BP | TBDNE |
|---|---|---|---|---|---|
| 38479-33-org | 273 | 0.8 | 0.1 | 98.6 | 0.5 |
| 38479-35-org | 274 | 0.6 | 1.0 | 98.3 | 0.1 |
| 38585-2-org  | 277 | 0.8 | 1.1 | 97.1 | 1.0 |
| 38585-3-org  | 278 | 0.7 | 0.3 | 97.8 | 1.2 |
| 38585-5-org  | 279 | 0.9 | 0.3 | 98.6 | 0.2 |
| 38585-6-org  | 279 | 0.8 | 0.6 | 98.3 | 0.3 |

*Weight percent for NM and area percent for DBNM, BP, and TBDNE.
NM = nitromethane, DBNM = dibromonitromethane [$CHBr_2NO_2$], BP = bromopicrin, TBDNE = tetrabromodinitroethane [$C_2Br_4(NO_2)_2$] or [$NO_2Br_2C—CBr_2NO_2$].

From the results using the laboratory scale 1 liter size chemical reactor, it is seen that the selectivity of the reaction to form bromopicrin was more than 97 percent, and the yield was 92.6±1.0 percent, when the reaction temperature (reaction temperature ($T_R$)) throughout adding of the aqueous solution of the sodium hydroxide to the mixture of water, nitromethane, and bromine, and consequently, throughout forming the reaction mixture containing bromopicrin, was maintained in a range of between about 24° C. and about 39° C. It is noted that the reaction temperature (reaction temperature ($T_R$)) in the higher range of between about 42° C. and about 48° C. did not reduce the selectivity or the yield of bromopicrin.

The main secondary products typically contained in the aqueous phase were the inorganic salt sodium bromide [NaBr]; the bromine-containing inorganic oxidants [$NaBrO$], [$NaBrO_2$], and [$NaBrO_3$]; and traces of the organic materials [$CBr_3NO_2$], [$CNaBr_2NO_2$], [$CHNaBrNO_2$], and [$CH_2NaNO_2$].

The collected aqueous phase was chemically treated using an aqueous solution of sodium hydrogen sulphite (SBS)—sodium bisulfate [$NaHSO_3$], which neutralized or/and reduced the bromine-containing inorganic oxidants.

Due to the presence of [$NaHSO_4$] and hydrobromic acid (hydrogen bromide) [HBr], along with a decrease in pH down to about 1, the acidity of the chemically treated aqueous phase was neutralized using the 34-35 weight percent aqueous solution of sodium hydroxide. The [$NaHSO_4$] and hydrobromic acid [HBr] present in the chemically treated aqueous phase reacted with the sodium hydroxide to form [NaBr], [$Na_2SO_3$], and [$Na_2SO_4$], in the resulting neutralized chemically treated aqueous phase, along with increasing the pH thereof to a value in a range of between about 6 and about 12.

TABLE 3

Analysis of the aqueous phase before and after chemical treatment (T).

| Sample no. | Weight grams | Oxidants as $BrO^-$ | $SO_3^{-2}$ percent | pH | $Na^+$ percent | $Br^-$ percent | TOC ppm |
|---|---|---|---|---|---|---|---|
| 38479-33-aq   | 781 | 3.7 | —    | 5.0  | 9.7 | 32.0 | 333 |
| 38479-33-aq-T | 917 | —   | 0.26 | 6.5  | 9.9 | 29.8 | 323 |
| 38479-35-aq   | 769 | 3.3 | —    | 4.7  | 9.4 | 32.7 | 253 |
| 38479-35-aq-T | 897 | —   | 0.26 | 5.7  | 9.8 | 30.2 | 247 |
| 38585-2-aq    | 763 | 3.1 | —    | 4.9  | 8.4 | 34.5 | 260 |
| 38585-2-aq-T  | 945 | —   | 0.17 | 7.3  | 7.9 | 29.6 | 254 |
| 38585-3-aq    | 762 | 3.0 | —    | 4.9  | 9.2 | 32.3 | 234 |
| 38585-3-aq-T  | 943 | —   | 0.24 | 5.9  | 9.0 | 28.8 | 173 |
| 38585-5-aq    | 743 | 3.0 | —    | 4.6  | 9.5 | 33.0 | 300 |
| 38585-5-aq-T  | 927 | —   | 0.18 | 11.9 | 8.5 | 28.7 | 277 |
| 38585-6-aq    | 742 | 3.0 | —    | 4.7  | 9.6 | 34.9 | 263 |
| 38585-6-aq-T  | 955 | —   | 0.02 | 8.7  | 8.9 | 28.0 | 237 |

For the data of Table 3, in order to guarantee full reduction of the oxidants, an excess of about 15 percent of the calculated amount of reductant was taken. TOC=total organic carbon. ppm=parts per million.

Figure 2:
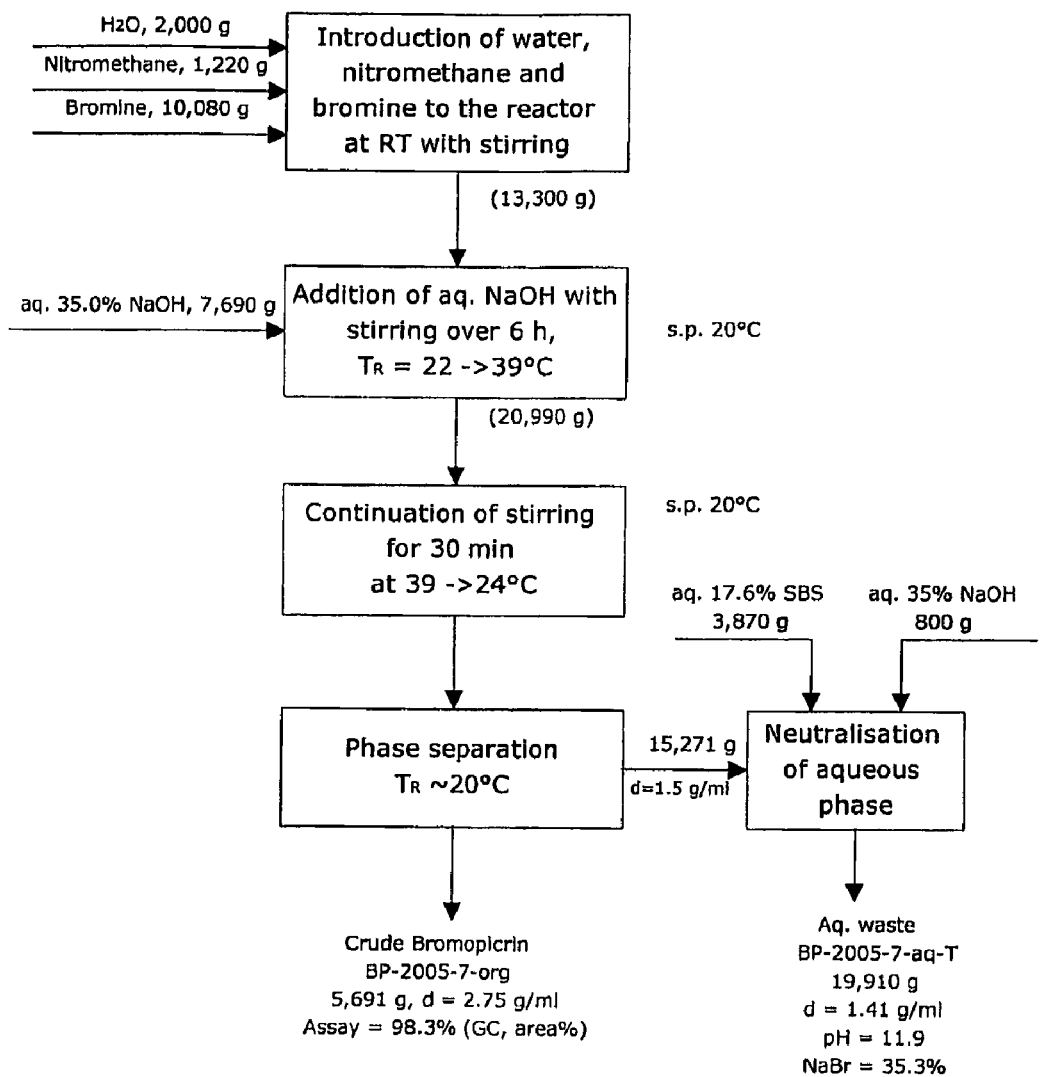
FIG. 2 is a flow block diagram of the actual scheme and procedures of an example of implementing the present invention on the mini-pilot plant scale, using a 16 liter size chemical reactor, for reaction conditions and results of an exemplary run, Run no. BP-2005-7, as described in the Examples, in accordance with the present invention.

Mini-Pilot Plant Scale (16 Liter Size Chemical Reactor):

Weights of starting materials (reactants) and products, and reaction conditions, are listed in Table 4. Composition analysis of the collected heavier (lower) organic phase (containing bromopicrin) of the reaction mixture is listed in Table 5. In Table 5, purity of the bromopicrin (BP) is listed in terms of weight percent, corresponding to the ratio of the weight of bromopicrin in the (collected) organic phase and the total weight of the (collected) organic phase. Composition analysis of the collected lighter (upper) aqueous phase (containing water and secondary products) of the reaction mixture, before and after chemical treatment, is listed in Table 6. FIG. 2 is a flow block diagram of the actual scheme and procedures of an example of implementing the present invention using the mini-pilot plant scale 16 liter chemical reactor, for reaction conditions and results of an exemplary run, Run no. 2005-7 (indicated in bold in Tables 4, 5, and 6). In FIG. 2, g=grams; %=percent; h=hours; RT=room temperature; s.p.=temperature set point; org=organic; aq.=aqueous; d=density; ml=milliliter; Assay=purity; and T=treated.

to about 1, the acidity of the chemically treated aqueous phase was neutralized using the 34-35 weight percent aqueous solution of sodium hydroxide. The [$NaHSO_4$] and hydrobromic acid [HBr] present in the chemically treated aqueous phase reacted with the sodium hydroxide to form [NaBr], [$Na_2SO_3$], and [$Na_2SO_4$], in the resulting neutralized chemically treated aqueous phase, along with increasing the pH thereof to a value in a range of between about 7 and about 12.

TABLE 4

Weights of starting materials and products, and reaction conditions.

| Run no. BP-2005- | $H_2O$ kg | NM kg | $Br_2$ kg | Aq. NaOH percent | Aq. NaOH kg | $T_R$ °C. | Time hours | Crude BP kg | Aq. phase kg |
|---|---|---|---|---|---|---|---|---|---|
| 1 | 2.00 | 1.22 | 9.98 | 35.0 | 7.65 | 25-40 | 4.0 | 5.64 | 15.15 |
| 2 | 2.00 | 1.22 | 10.05 | 35.1 | 7.75 | 35-38 | 4.0 | 5.64 | 15.35 |
| 3 | 2.00 | 1.22 | 10.00 | 35.1 | 7.65 | 22-39 | 4.0 | 5.65 | 15.19 |
| 4 | 2.00 | 1.22 | 10.02 | 35.1 | 7.70 | 23-39 | 4.0 | 5.65 | 15.25 |
| 5 | 2.00 | 1.22 | 10.00 | 35.1 | 7.77 | 25-45 | 4.5 | 5.58 | 15.27 |
| 6 | 2.00 | 1.22 | 10.08 | 35.0 | 7.72 | 25-45 | 4.0 | 5.68 | 15.28 |
| 7 | 2.00 | 1.22 | 10.08 | 35.0 | 7.69 | 22-39 | 6.0 | 5.69 | 15.27 | kg = kilograms. $T_R$ = temperature of the reaction (reaction temperature).
NM = nitromethane, BP = bromopicrin.

TABLE 5

Analysis of the organic phase (containing bromopicrin).

| Sample no. BP-2005- | Weight kg | Composition, percent by GC* | | | |
|---|---|---|---|---|---|
| | | NM | DBNM | BP | TBDNE |
| 1-org | 5.64 | <1.0 | 0.6 | 98.4 | n.d. |
| 2-org | 5.64 | <1.0 | 0.8 | 98.2 | n.d. |
| 3-org | 5.65 | <1.0 | 0.7 | 98.3 | n.d. |
| 4-org | 5.65 | <1.0 | n.d. | 99.0 | n.d. |
| 5-org | 5.58 | <1.0 | 0.3 | 98.7 | n.d. |
| 6-org | 5.68 | <1.0 | 0.3 | 98.7 | n.d. |
| 7-org | 5.69 | <1.0 | 0.7 | 98.3 | n.d. |

*Weight percent for NM and area percent for DBNM, BP, and TBDNE.
NM = nitromethane, DBNM = dibromonitromethane [$CHBr_2NO_2$], BP = bromopicrin, TBDNE = tetrabromodinitroethane [$C_2Br_4(NO_2)_2$] or [$NO_2Br_2C$—$CBr_2NO_2$].

From the results using the laboratory scale 1 liter size chemical reactor, it is seen that the selectivity of the reaction to form bromopicrin was more than 98 percent, and the yield was 94.5±1.0 percent, when the reaction temperature (reaction temperature ($T_R$)) throughout adding of the aqueous solution of the sodium hydroxide to the mixture of water, nitromethane, and bromine, and consequently, throughout forming the reaction mixture containing bromopicrin, was maintained in a range of between about 22° C. and about 40° C. It is noted that the reaction temperature (reaction temperature ($T_R$)) being about 45° C. did not reduce the selectivity or the yield of bromopicrin, but the yield of bromopicrin was about 93 percent.

The main secondary products typically contained in the aqueous phase were the inorganic salt sodium bromide [NaBr]; the bromine-containing inorganic oxidants [NaBrO], [$NaBrO_2$], and [$NaBrO_3$]; and traces of the organic materials [$CBr_3NO_2$], [$CNaBr_2NO_2$], [$CHNaBrNO_2$], and [$CH_2NaNO_2$].

The collected aqueous phase was chemically treated using an aqueous solution of sodium hydrogen sulphite (SBS)—sodium bisulfate [$NaHSO_3$], which neutralized or/and reduced the bromine-containing inorganic oxidants.

Due to the presence of [$NaHSO_4$] and hydrobromic acid (hydrogen bromide) [HBr], along with a decrease in pH down

TABLE 6

Analysis of the aqueous phase before and after chemical treatment (T).

| Sample no. BP-2005- | Weight kg | Oxidants as $BrO^-$ | $SO_3^{-2}$ percent | pH | $Na^+$ percent | $Br^-$ percent |
|---|---|---|---|---|---|---|
| 1-aq | 15.15 | 3.23 | — | 4.7 | 10.5 | 34.7 |
| 1-aq-T | 19.78 | — | 0.37 | 7.5 | 8.8 | 27.3 |
| 2-aq | 15.35 | 3.39 | — | 4.6 | 10.4 | 35.5 |
| 2-aq-T | 19.62 | — | 0.21 | 10.4 | 9.1 | 26.5 |
| 3-aq | 15.19 | 3.19 | — | 4.5 | 10.4 | 34.4 |
| 3-aq-T | 19.90 | — | 0.37 | 10.9 | 9.3 | 26.7 |
| 4-aq | 15.25 | 3.37 | — | 4.5 | 10.4 | 34.6 |
| 4-aq-T | 19.93 | — | 0.29 | 12.0 | 9.4 | 27.0 |
| 5-aq | 15.27 | 3.51 | — | 4.5 | 10.2 | 34.4 |
| 5-aq-T | 20.46 | — | 0.27 | 10.8 | 9.2 | 26.8 |
| 6-aq | 15.28 | 3.26 | — | 4.5 | 10.0 | 34.2 |
| 6-aq-T | 20.20 | — | 0.26 | 11.9 | 9.3 | 26.7 |
| 7-aq | 15.27 | 3.12 | — | 4.8 | 10.9 | 34.7 |
| 7-aq-T | 19.91 | — | 0.28 | 11.9 | 9.6 | 27.4 |

For the data of Table 6, in order to guarantee full reduction of the oxidants, an excess of about 15 percent of the calculated amount of reductant was taken.

The process of preparing bromopicrin, and the high purity bromopicrin prepared therefrom, of the present invention, as illustratively described and exemplified hereinabove, have several beneficial and advantageous aspects, characteristics, or features, which are based on, in addition to, or a consequence of, the above described main aspects of novelty and inventiveness.

First, the process of preparing bromopicrin of the present invention provides an industrially applicable, reproducible, safe, environmentally friendly, and cost effective, way of producing bromopicrin in near quantitative (theoretical stoichiometric) yield of bromopicrin having a purity equal to or greater than 96 percent, and as high as 99 weight percent (weight bromopicrin/total weight of the organic phase).

Second, the process of preparing bromopicrin of the present invention includes an industrially applicable, reproducible, safe, environmentally friendly, and cost effective, procedure for collecting the high purity bromopicrin produced therefrom. The organic phase containing the bromopicrin is directly collected, in particular, via gravity (e.g., by free or forced draining or pumping), from the reaction mixture, without subjecting the organic phase to distillation or extraction, for obtaining near quantitative (theoretical stoichiometric) yield of bromopicrin having a purity equal to or greater than 96 weight percent, and as high as 99 weight percent. This aspect results in precluding the need for including a distillation or extraction procedure along with relatively expensive distillation or extraction equipment, as well as costs involved for operating and maintaining thereof. This aspect also results in precluding the need for handling and taking into account the affects, in particular, as relating to health and safety, of the potentially hazardous (highly energetic) bromopicrin product during distillation or extraction conditions, as well as of the potentially hazardous and waste generating extraction solvent.

Third, in the process of preparing bromopicrin, providing the mixture of nitromethane and bromine is performed without adding any organic solvent to the nitromethane and bromine, so that the mixture is substantially absent of an organic solvent. Accordingly, in the process, there is no organic solvent in the initial mixture of nitromethane and bromine, or in the subsequent reaction mixture containing the bromopicrin formed therefrom. This aspect of the present invention results in precluding the possibility of introducing impurities or/and undesirable reaction intermediates and by-products into the process due to the presence of an organic solvent, and precluding the need for handling and taking into account the affects, in particular, as relating to health and safety, of using an organic solvent during any stage of the process of preparing the bromopicrin.

Thus, the present invention successfully addresses and overcomes several shortcomings and limitations, and widens the scope, of presently known techniques used for preparing bromopicrin, and is readily commercially applicable.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A process of preparing bromopicrin, the process comprising:
    providing a mixture of nitromethane and bromine;
    subsequent to said providing, adding an aqueous solution of an alkaline substance to said mixture, to thereby provide a reaction mixture containing the bromopicrin, said adding being performed such that no excess of said alkaline substance occurs in said reaction mixture during said adding; and
    collecting the bromopicrin from said reaction mixture by free or forced draining or pumping of organic phase from said reaction mixture.

2. The process of claim 1, wherein said providing said mixture of said nitromethane and said bromine is performed such that said mixture is substantially absent of an organic solvent.

3. The process of claim 1, wherein during said providing said mixture of said nitromethane and said bromine, temperature of said mixture is in a range of between about 10° C. and about 50° C.

4. The process of claim 1, wherein during said providing said mixture of said nitromethane and said bromine, temperature of said mixture is in a range of between about 20° C. and about 25° C.

5. The process of claim 1, wherein said providing said mixture is performed using a molar ratio of bromine and nitromethane in a range of between about 3 and about 4.

6. The process of claim 1, wherein said providing said mixture is performed using a molar ratio of bromine and nitromethane in a range of between about 3 and about 3.5.

7. The process of claim 1, wherein said mixture of said nitromethane and said bromine further includes water.

8. The process of claim 7, wherein said providing said mixture is performed according to a sequence of adding said nitromethane to said water, followed by adding said bromine to said nitromethane and said water, thereby forming said mixture.

9. The process of claim 7, wherein said providing said mixture is performed using a weight ratio of said nitromethane and said water in a range of between about 0.25 and about 4.

10. The process of claim 7, wherein said providing said mixture is performed using a weight ratio of said nitromethane and said water in a range of between about 0.5 and about 2.

11. The process of claim 1, wherein said alkaline substance is selected from the group consisting of metal alkali hydroxides, alkaline earth hydroxides, and combinations thereof.

12. The process of claim 11, wherein said metal alkali hydroxide is selected from the group consisting of lithium hydroxide, sodium hydroxide, potassium hydroxide, and a combination thereof.

13. The process of claim 11, wherein said metal alkali hydroxide is selected from the group consisting of sodium hydroxide, potassium hydroxide, and a combination thereof.

14. The process of claim 12, wherein said alkaline substance is said sodium hydroxide.

15. The process of claim 11, wherein said alkaline earth hydroxide is selected from the group consisting of magnesium hydroxide, calcium hydroxide, strontium hydroxide, and barium hydroxide.

16. The process of claim 1, wherein a concentration of said alkaline substance in said aqueous solution of said alkaline substance is in a range of between about 5 weight percent and about 50 weight percent (weight said alkaline substance/ weight said aqueous solution).

17. The process of claim 1, wherein a concentration of said alkaline substance in said aqueous solution of said alkaline substance is in a range of between about 25 weight percent and about 40 weight percent (weight said alkaline substance/ weight said aqueous solution).

18. The process of claim 1, wherein a concentration of said alkaline substance in said aqueous solution of said alkaline substance is about 35 weight percent (weight said alkaline substance/weight said aqueous solution).

19. The process of claim 1, wherein prior to said adding said aqueous solution to said mixture, temperature of said mixture is in a range of between about 10° C. and about 50° C.

20. The process of claim 1, wherein temperature of said reaction mixture maintained throughout said adding of said aqueous solution to said mixture is in a range of between about 20° C. and about 50° C.

21. The process of claim 1, wherein temperature of said reaction mixture maintained throughout said adding of said aqueous solution to said mixture is in a range of between about 35° C. and about 45° C.

22. The process of claim 1, wherein said adding said aqueous solution to said mixture is performed during a time period in a range of between about 0.5 hour and about 24 hours.

23. The process of claim 1, wherein said adding said aqueous solution to said mixture is performed during a time period in a range of between about 1 hour and about 10 hours.

24. The process of claim 1, wherein said adding said aqueous solution to said mixture is performed during a time period in a range of between about 2 hours and about 6 hours.

25. The process of claim 1, wherein following said collecting the bromopicrin, there is collecting aqueous phase from said reaction mixture and chemically treating said aqueous phase, thereby providing a treated form of said aqueous phase.

26. The process of claim 25, wherein said treated form of said aqueous phase is used in a procedure for isolating sodium bromide, producing bromine, or producing hydrobromic acid.

* * * * *